(12) United States Patent
Barrett et al.

(10) Patent No.: US 12,247,906 B2
(45) Date of Patent: Mar. 11, 2025

(54) PARTICLE EMISSION TOMOGRAPHY

(71) Applicants: Arizona Board of Regents on Behalf of the University of Arizona, Tucson, AZ (US); inviCro, LLC, Boston, MA (US)

(72) Inventors: Harrison H. Barrett, Tucson, AZ (US); Yijun Ding, Tucson, AZ (US); Luca Caucci, Tucson, AZ (US); John William Hoppin, Boston, MA (US)

(73) Assignees: Arizona Board of Regents on behalf of the University of Arizona, Tucson, AZ (US); inviCro, LLC, Boston, MA (US)

(*) Notice: Subject to any disclaimer, the term of this patent is extended or adjusted under 35 U.S.C. 154(b) by 0 days.

(21) Appl. No.: 17/506,396

(22) Filed: Oct. 20, 2021

(65) Prior Publication Data
US 2022/0187181 A1    Jun. 16, 2022

Related U.S. Application Data

(63) Continuation of application No. 16/653,922, filed on Oct. 15, 2019, now Pat. No. 11,249,000, which is a (Continued)

(51) Int. Cl.
*G01N 15/02* (2024.01)
*A61B 6/00* (2006.01)
(Continued)

(52) U.S. Cl.
CPC ......... *G01N 15/0227* (2013.01); *A61B 6/037* (2013.01); *A61B 6/4241* (2013.01); (Continued)

(58) Field of Classification Search
CPC .... G01N 15/0227; G01N 15/02; A61B 6/037; A61B 6/4241; A61B 6/4258; A61B 6/5205; G01B 7/004; G01T 1/2942
See application file for complete search history.

(56) References Cited

U.S. PATENT DOCUMENTS

| 4,111,191 A | 9/1978 | Shaw |
| 4,595,014 A | 6/1986 | Barrett et al. |

(Continued)

FOREIGN PATENT DOCUMENTS

WO    2004/104634    12/2004

OTHER PUBLICATIONS

Aarsvold et al. (1996) "Symmetries of single-slice multiple-pinhole tomographs," IEEE Nucl. Sci. Symp. Conf. Rec. 3:1673-1677.
(Continued)

*Primary Examiner* — Mekonen T Bekele
(74) *Attorney, Agent, or Firm* — LEYDIG, VOIT & MAYER, LTD.

(57) ABSTRACT

The present invention provides autoradiography methods and systems for imaging via the detection of alpha particles, beta particles, or other charged particles. Embodiments of the methods and systems provide high-resolution 3D imaging of the distribution of a radioactive probe, such as a radiopharmaceutical, on a tissue sample. Embodiments of the present methods and systems provide imaging of tissue samples by reconstruction of a 3D distribution of a source of particles, such as a radiopharmaceutical. Embodiments of the methods and systems provide tomographic methods including microtomography, macrotomography, cryomicrotomography and cryomacrotomography.

13 Claims, 24 Drawing Sheets

Related U.S. Application Data continuation of application No. 15/526,514, filed as application No. PCT/US2015/060198 on Nov. 11, 2015, now Pat. No. 10,444,136.

(60) Provisional application No. 62/199,904, filed on Jul. 31, 2015, provisional application No. 62/078,562, filed on Nov. 12, 2014.

(51) Int. Cl.
| | |
|---|---|
| *A61B 6/03* | (2006.01) |
| *A61B 6/42* | (2024.01) |
| *G01B 7/004* | (2006.01) |
| *G01N 15/0227* | (2024.01) |
| *G01T 1/29* | (2006.01) |

(52) U.S. Cl.
CPC .......... *A61B 6/4258* (2013.01); *A61B 6/5205* (2013.01); *G01B 7/004* (2013.01); *G01N 15/02* (2013.01); *G01T 1/2942* (2013.01)

(56) References Cited

U.S. PATENT DOCUMENTS

| | | | |
|---|---|---|---|
| 5,245,191 | A | 9/1993 | Barber et al. |
| 5,825,033 | A | 10/1998 | Barrett et al. |
| 7,113,958 | B1 | 9/2006 | Lantrip et al. |
| 7,820,977 | B2 | 10/2010 | Beer et al. |
| 8,536,527 | B2 | 9/2013 | Morris et al. |
| 9,823,364 | B2 | 11/2017 | Barrett et al. |
| 9,977,136 | B2 | 5/2018 | Barrett et al. |
| 10,444,136 | B2 | 10/2019 | Barrett et al. |
| 11,249,000 | B2 | 2/2022 | Barrett et al. |
| 2004/0054248 | A1 | 3/2004 | Kimchy et al. |
| 2007/0156047 | A1 | 7/2007 | Nagler et al. |
| 2007/0249943 | A1 | 10/2007 | Texier-Nogues et al. |
| 2008/0033291 | A1 | 2/2008 | Rousso et al. |
| 2008/0056435 | A1 | 3/2008 | Basu et al. |
| 2008/0128626 | A1 | 6/2008 | Rousso et al. |
| 2008/0260228 | A1 | 10/2008 | Dichterman et al. |
| 2009/0045348 | A1 | 2/2009 | Stuenkel et al. |
| 2009/0050811 | A1 | 2/2009 | Barrett et al. |
| 2009/0078875 | A1* | 3/2009 | Rousso .......... A61B 6/583 250/363.04 |
| 2009/0125242 | A1 | 5/2009 | Choi et al. |
| 2010/0140487 | A1 | 6/2010 | Barrett et al. |
| 2011/0186720 | A1* | 8/2011 | Jongen .......... G01T 1/1642 250/361 R |
| 2012/0307250 | A1 | 12/2012 | Wang et al. |
| 2013/0238291 | A1* | 9/2013 | Schultz .......... G01N 23/207 703/2 |
| 2017/0010369 | A1 | 1/2017 | Barrett et al. |
| 2017/0343460 | A1 | 11/2017 | Barrett et al. |
| 2018/0052242 | A1 | 2/2018 | Barrett et al. |

OTHER PUBLICATIONS

Anger (1958) "Scintillation camera," Rev. Sci. Instrum. 29:27-33.
Barrett et al. (1991) "Null functions and eigenfunctions: tools for the analysis of imaging systems," Prog. Clin. Biol. Res. 363:211-226.
Barrett et al. (1997) "List-mode likelihood," J. Opt. Soc. Am. A. 14:2914-2923.
Barrett et al. (2009) "Maximum-likelihood methods for processing signals from gamma-ray detectors," IEEE Trans. Nucl. Sci. 56(3):725-735.
Barrett et al. (Sep. 12, 2014) "Radiance and photon noise: imaging in geometrical optics, physical optics, quantum optics, and radiology," Proc. SPIE. 9193:919302. pp. 1-17.
Barrett et al. (Jan. 21, 2015) "Task-based measures of image quality and their relation to radiation dose and patient risk," Phys. Med. Biol., 60(2):R1-75.
Berger et al. (Last Updated Jul. 28, 2017) "Stopping-power and range tables for electrons, protons, and helium ions," Project No. NISTIR 4999. NIST Physics Laboratory. Accessible on the Internet at URL: https://www.nist.gov/pml/stopping-power-range-tables-electrons-protons-and-helium-ions, 33 pgs. [Last Accessed Jan. 19, 2018].
Bora et al. (Feb. 2015) "Impact of the Fano factor on position and energy estimation in scintillation detectors," IEEE Trans. Nucl. Sci. 62:42-56.
Bouwens et al. (2001) "LMIRA: list-mode iterative reconstruction algorithm for Spect," IEEE Trans. Nucl. Sci. 48(4): 1364-1370.
Caucci et al. (2009) "Maximum likelihood event estimation and list-mode image reconstruction on GPU hardware," In; The Proceedings of the 2009 IEEE Nuclear Science Symposium Conference Record (NSS/MIC), Oct. 24-Nov. 1, 2009, Orlando, FL, USA. pp. 4072-4076.
Caucci et al.(2010) "List-mode MLEM image reconstruction from 3D ML position estimates," IEEE Nucl. Sci. Symp. Conf. Rec. pp. 2643-2647.
Caucci et al. (2012) "Objective assessment of image quality. V. Photon-counting detectors and list-mode data," J. Opt. Soc. Am. A. 29(6):1003-1016.
Caucci et al. (Jan. 2016) "Radiance and photon noise: imaging in geometrical optics, physical optics, quantum optics and radiology," Optical Engineering. 55(1):013102. pp. 1-13.
Clarkson et al. (2010) "SVD for imaging systems with discrete rotational symmetry," Opt. Express. 18(24):25306-25320.
Davison et al. (1981) "Tomographic reconstruction with arbitrary directions," Comm. Pure Appl. Math. 34(1):77-119.
Defrise et al. (2005) "Fourier rebinning of time-of-flight PET data," Phys. Med. Biol. 50(12):2749-63.
Ding et al. (Nov. 2014) "αET : Alpha Emission Tomography," In; The Proceedings of the 2014 IEEE Nuclear Science Symposium and Medical Imaging Conference, Nov. 8-15, 2014, Seattle, WA, USA. pp 1-3.
Eskin (1997) "Semiconductor gamma-ray imaging detectors for nuclear medicine," PhD Thesis University of Arizona, Tucson, AZ, USA.
Furenlid et al. (2000) "Spatial pileup considerations for pixelated gamma-ray detectors," IEEE Transactions on Nuclear Science. 47(4):1399-1403.
Furenlid et al. (2004) "FastSPECT II: A second-generation high-resolution dynamic SPECT imager," IEEE Trans. Nucl. Sci. 51:631-635.
Furenlid et al. (2005) "Real-time data acquisition and maximum-likelihood estimation for gamma cameras," IEEE NPSS Real Time Conf. pp. 498-501.
Furenlid et al. (2008) "Adaptive small-animal SPECT/CT," In; The Proceedings of the 5th IEEE International Symposium on Biomedical Imaging: From Nano to Macro, 2008. ISBI 2008, May 14-17, 2008, Paris, France. pp. 1407-1410.
Granja et al. (Dec. 2013) "Energy loss and online directional track visualization of fast electrons with the pixel detector timepix," Radiation Measurements. 59:245-261.
Gullberg et al. (1994) "A reconstruction algorithm using singular value decomposition of a discrete representation of the exponential radon transform using natural pixels," IEEE Trans. Nucl. Sci. 41:2812-2819.
Hesterman et al. (2010) "Maximum-likelihood estimation with a contracting-grid search algorithm," IEEE Trans. Nucl. Sci. 57(3):1077-1084.
International Search Report with Written Opinion corresponding to International Patent Application No. PCT/US2015/060198, mailed Jan. 28, 2016.
Jakubek et al. (2008) "Pixel detectors for imaging with heavy charged particles," Nuclear Instruments and Methods in Physics Research Section A: Accelerators, Spectrometers, Detectors and Associated Equipment. 591(1):155-158.
Jha et al. (2012) "Three-dimensional Neumann-series approach to model light transport in nonuniform media," J. Opt. Soc. Am. A. 29(9):1885-1899.

(56) References Cited

OTHER PUBLICATIONS

Jha (Mar. 2013) "Retrieving information from scattered photons in medical imaging," PhD Thesis College of Optical Sciences, University of Arizona, Tucson, AZ, USA.

Jha et al. (Jun. 2013) "Analytic methods for list-mode reconstruction," In; The Proceedings of the 12th International Meeting on Fully Three-Dimensional Image Reconstruction in Radiology and Nuclear Medicine, Jun. 16-21, 2013. Lake Tahoe, California. pp. 94-97.

Jha et al. (Sep. 21, 2015) "Singular value decomposition for photon-processing nuclear imaging systems and applications for reconstruction and computing null functions," Phys Med Biol. 60(18):7359-7385.

Kadrmas et al. (1996) "An SVD investigation of modeling scatter in multiple energy windows for improved SPECT images," IEEE Trans. Nucl. Sci. 43(3):2275-2284.

Khurd et al. (2004) "A globally convergent regularized ordered-subset EM algorithm for list-mode reconstruction," IEEE Trans. Nuc. Sci. 51:719-725.

King et al. (1984) "Two-dimensional filtering of SPECT images using the Metz and Wiener filters," J. Nucl. Med. 25(11):1234-1240.

Kupinski et al. (Mar. 2013) "Scanning linear estimation: improvements over region of interest (ROI) methods," Phys. Med. Biol. 58(5):1283-1301.

Lehovich (2005) "List mode SPECT Reconstruction using empirical likelihood," PhD Thesis College of Optical Sciences, University of Arizona, Tucson, AZ, USA.

Madsen (2007) "Recent Advances in SPECT Imaging," J. Nucl. Med. 48(4):661- 672.

Marks et al. (1999) "Improving performance of a CdZnTe imaging array by mapping the detector with gamma rays," Nuclear Instruments and Methods in Physics Research Section A: Accelerators, Spectrometers, Detectors and Associated Equipment. 428(1): 102-112.

Miller et al. (2008) "Recent advances in BazookaSPECT: Real-time data processing and the development of a gamma-ray microscope," Nuclear Instruments and Methods in Physics Research Section A: Accelerators, Spectrometers, Detectors and Associated Equipment. 591(1):272-275.

Miller et al. (2009) "Progress in BazookaSPECT," Proc. SPIE. 7450:74500C.

Miller et al. (2009) "System integration of FastSPECT III, a dedicated SPECT rodent-brain imager based on BazookaSPECT detector technology," IEEE Nuclear Science Symp. Conf. Rec. pp. 4004-08.

Miller et al. (Dec. 11, 2014) "The iQID camera: An ionizing-radiation quantum imaging detector," Nuclear Instruments and Methods in Physics Research Section A: Accelerators, Spectrometers, Detectors and Associated Equipment. 767:146-152.

Moore et al. (2012) "ModPET - A compact PET system employing modular gamma cameras, maximum-likelihood event-parameter estimation, and list-mode ML-EM reconstruction," J. Nucl. Med. Vol. 53. Suppl 1. Abstract No. 491.

Park et al. (2009) "Singular vectors of a linear imaging system as efficient channels for the Bayesian ideal observer," IEEE Trans. Med. Imaging. 28(5):657-668.

Parra et al. (1998) "List-mode likelihood: EM algorithm and image quality estimation demonstrated on 2-D Pet," IEEE Trans. Med. Imaging. 17:228-235.

Paxman et al. (1985) "Image reconstruction from coded data: II. Code design," J. Opt. Soc. Am. A. 2(4):501-509.

Peterson et al. (Sep. 2011) "SPECT detectors: the Anger Camera and beyond," Phys. Med. Biol. 56(17): R145-182.

Reader et al. (2002) "One-pass list-mode EM algorithm for high-resolution 3-D Pet image reconstruction into large arrays," IEEE Trans. Nuc. Sci. 49(3):693-699.

Reader et al. (2007) "Advances in PET image reconstruction," PET Clinics. 2(2):173-190.

Sand et al. (2010) "Remote Optical Detection of Alpha Radiation," Document No. IAEA-CN-184/23. In; The Proceedings of the Symposium on International Safeguards: Preparing for Future Verification Challenges. Vienna, Austria, Nov. 1-5, 2010. Accessible on the Internet at URL: https://www.iaea.org/safeguards/symposium/2010/Documents/PapersRepository/023.pdf.

Schretter (2009) "Event-by-event image reconstruction from list-mode PET data," IEEE Trans. Img. Proc. 18(1):117-124.

Shepp et al. (1974) "The Fourier reconstruction of a head section," IEEE Trans. Nucl. Sci. 21:21-43.

Soesbe et al. (2010) "High Resolution Photon Counting Using a Lens-Coupled EMCCD Gamma Camera," IEEE Transactions on Nuclear Science. 57(3):958-963.

Taguchi et al. (Oct. 2013) "Vision 20/20: Single photon counting x-ray detectors in medical imaging," Med. Phys. 40(10):100901.

Wilson et al. (1998) "Decomposition of images and objects into measurement and null components," Opt. Express. 2(6):254-260.

Zeng et al. (1997) "An SVD study of truncated transmission data in SPECT," IEEE Trans. Nucl. Sci. 44(1):107-111.

\* cited by examiner

Incident alpha particle interacts with the sensor and generates charges along its track Semiconductor senor with a depletion region thickness 5~50 um and pixel pitch 0.1~20 um

PARTICLE EMISSION TOMOGRAPHY

CROSS-REFERENCE TO RELATED APPLICATIONS

This application is a continuation of U.S. application Ser. No. 16/653,922, filed Oct. 15, 2019, which is a continuation of U.S. application Ser. No. 15/526,514, filed May 12, 2017 (now issued as U.S. Pat. No. 10,444,136), which was a national stage application under 35 U.S.C. § 371 of International Application No. PCT/US2015/060198, filed Nov. 11, 2015, which claims the benefit of priority from U.S. Provisional Patent Application No. 62/078,562, filed Nov. 12, 2014, and U.S. Provisional Application No. 62/199,904, filed on Jul. 31, 2015, each of which is hereby incorporated by reference in its entirety to the extent not inconsistent herewith.

STATEMENT REGARDING FEDERALLY SPONSORED RESEARCH OR DEVELOPMENT

This invention was made with government support under Grant Nos. R01 EB000803 and P41 EB002035 awarded by National Institutes of Health. The government has certain rights in the invention.

BACKGROUND

Autoradiography is a well-developed technique for imaging in the context of clinical medicine and research on biological processes. In this technique, a radioactive probe is administered to a patient or a subject or a tissue to provide an internal source of radiation, thus distinguishing this method from conventional radiography in which an external source of radiation is employed. Autoradiography is most commonly used for imaging of ex vivo samples obtained from tissue administered with a radioactive pharmaceutical. Thin slices (e.g., 5-50 µm thick) of the sample are subsequently analyzed using a high—resolution imaging detector sensitive to charged particles (e.g., alpha particles, beta particles and/or Auger electrons) emitted by the radioactive pharmaceutical. These techniques provide 2D images exhibiting high spatial resolution capable of resolving the distribution of a radioactive pharmaceutical at the cellular or subcellular level.

Although autoradiography provides a valuable approach for high-resolution imaging of tissue, this technique is significantly limited in its extension to 3D imaging of in vivo tissue. While reassembly of 2D slice image information to obtain a 3D image of a sample is feasible, this application of autoradiography is labor intensive and practically limited due to distortion of thin film slices introduced by dehydration and/or in transferring them to an imaging detector. Further, extension of conventional autoradiography to 3D imaging requires sectioning of the sample into thin slices to provide depth information, thereby effectively limiting the technique to application of ex vivo tissue samples.

SUMMARY

The present invention provides autoradiography methods and systems for imaging via the detection of alpha particles, beta particles, or other charged particles. Embodiments of the methods and systems provide high-resolution 3D imaging of the distribution of a radioactive probe, such as a radiopharmaceutical, on a tissue sample. Embodiments of the present methods and systems provide imaging of tissue samples by reconstruction of a 3D distribution of a source of particles, such as a radiopharmaceutical. Embodiments of the methods and systems provide tomographic methods including microtomography, macrotomography, cryomicrotomography and cryomacrotomography.

The present invention provides autoradiography methods and devices for 3D imaging via the detection of beta particles or other charged particles. Embodiments of the present methods and systems provide high-resolution 3D imaging of the distribution of a radioactive probe, such as a radioactive pharmaceutical, in an intact, unsectioned tissue sample without the need for physically slicing the sample into sections. Embodiments of the present methods and systems provide for 3D imaging of in vivo tissue and ex vivo tissue via detection of particles from a single side of the sample. Embodiments of the present methods and systems provide for 3D imaging of living tissue including, for example, dynamic, time evolved imaging and characterization of a living tissue sample.

The disclosed systems and methods employ an autoradiographic imaging approach where particles emitted by a radioactive composition within the tissue are detected to provide a plurality of position dependent signals, for example, providing information characterizing individual trajectories of the detected particles. In some embodiments, a charged particle track detector is used to independently detect particles at a plurality of positions along their respective trajectories. For example, suitable track detectors include scintillator-based detectors, microchannel plate-based image intensifiers coupled to a thick scintillation material or semiconductor charge-coupled devices (CCD), active pixel sensors in complementary metal-oxide-semiconductor (CMOS), or N-type metal-oxide-semiconductor (NMOS, Live MOS) technologies or other video camera type detector where the sensitive region, active region or depletion region is thick enough to stop the particle. The recorded track can be analyzed to determine attributes of each track such as the point at which the charged particle entered the thick detector, the particle's direction at that point and the total energy deposited in that track. In embodiments, these attributes are used in an iterative tomographic reconstruction algorithm for accurate determination of a 3D image of the distribution of the source of particles within the tissue, for example, by determining positions and directions of the detected particles interacting with a charged particle track detector. In embodiments, characterization of the positions and directions of particles entering a detector provides information useful for determining a distribution of the source of particles within the tissue using various methods. In some embodiments, a particle transport algorithm is utilized, which estimates, simulates or otherwise accounts for propagation processes that take place between a location and the point at which the particle interacts with the detector. In some embodiments, for example, a maximum likelihood expectation maximization algorithm is used to accurately reconstruct a 3D image of the distribution of a radiopharmaceutical in a sample from the position dependent signals collected for the detected particles. Optionally, the devices and methods of the invention are useful for not only detecting beta particles, but other energetic particles, including alpha particles, conversion electrons, auger electrons, electron-like particles and/or positrons.

In an aspect, provided are methods of reconstructing a 3D distribution of a source of the particles. In a specific embodiment, the invention provides s method for reconstructing a 3D distribution of a source of particles, the method comprising the steps of: (1) providing the source of particles from within a tissue sample, wherein the particles comprise beta particles, alpha particles, positrons, or conversion electrons; (2) repeating, for each of a plurality of the particles from the source, the steps of: (a) detecting the particle with a particle-processing detector; (b) determining attributes of the particle; wherein the attributes include at least one of: (i) a two dimensional position corresponding to an interaction point where the particle interacts with the particle-processing detector; and (ii) an energy that is deposited in the particle-processing detector by the particle; and (3) storing the attributes of the particle; thereby generating attributes for each of the plurality of particles from the source; and (4) reconstructing the 3D distribution of the source of particles using at least a portion of the attributes for each of the plurality of particles. In an embodiment, a method of the invention includes determining both the attributes of: (i) a two dimensional position corresponding to an interaction point where the particle interacts with the particle-processing detector; and (ii) an energy that is deposited in the particle-processing detector by the particle In an embodiment, for example, the interaction point corresponds to a two-dimensional position that the particle interacts with an active area of the two-dimensional detector. In an embodiment, the interaction point corresponds to a two-dimensional position that the particle interacts with an entrance face of the two-dimensional detector. In certain embodiments, the energy is a total energy that is deposited on the two-dimensional detector by the particle. In embodiments, the attributes further comprise a particle interaction time, the energy of the particle upon interacting with the detector or a direction of travel of the particle.

In an exemplary embodiment, the provided method comprises a tomographic method, for example, microtomography, macrotomography, cryomicrotomography or cryomacrotomography. In certain embodiments, the source of particles is present within a tissue sample. In embodiments, the source of particles comprise a distribution of a radiopharmaceutical within the tissue sample. In certain embodiments, the method further comprises calculating the energy lost by the particle while traveling in the tissue sample. In certain embodiments, the method further comprises calculating the total distance traveled by the particle within the tissue.

In an exemplary embodiment, the provided method wherein a particle is emitted upon radioactive decay occurring in the tissue to be imaged, and has an initial energy that is known. In an embodiment, a particle is emitted upon radioactive decay occurring in the tissue to be imaged, and has an initial energy that is not known. In an embodiment, further comprising determining the energy and angle of the particle. In an embodiment, further comprising calculating an energy lost for each of the plurality of particles while traveling in the tissue sample. In an embodiment, a method further comprising calculating a distance traveled for each of the plurality of particles within the tissue sample from the energy lost by each of the particles.

In an exemplary embodiment, the provided method interaction point corresponds to a two-dimensional position that the particle interacts with an active area of the particle-processing detector. In an embodiment, a particle-processing detector is one that collects signals from multiple sensors (usually pixels) and uses them to estimate attributes of the particle interaction. In an embodiment, the interaction point corresponds to a two-dimensional position that the particle interacts with an entrance face of the particle-processing detector. In further embodiments, the attributes further comprises a particle interaction time, the energy of the particle upon interacting with the detector or a direction of travel of the particle. In an embodiment, the source of particles comprises a distribution of a radiopharmaceutical within the tissue sample.

In an exemplary embodiment, the provided method further comprising a step of administering the source of particles to a patient, subject or tissue, wherein the source of particles comprises a radiopharmaceutical. In embodiments, the 3D distribution of the source of particles comprises a distribution of the radiopharmaceutical in the tissue. In embodiments, the tissue is in vivo tissue or ex vivo tissue.

In embodiments, the method wherein the source of particles is provided in a tissue sample having a thickness selected from the range of 1 μm to 100 mm. In embodiments, the source of particles is located at a depth within a tissue selected from the range of 0 to 10 mm. In embodiments, the source of particles comprises radioactive compositions within living tissue. In embodiments, the source of particles is provided in a tissue sample having a thickness selected from the range of 1 μm to 100 μm. In embodiments, the source of particles is located at a depth within a tissue selected from the range of 0 to 10 μm. Exemplary particles include, but are not limited to, subatomic particles such as protons, neutrons and electrons, high-energy particles such as alpha particles and beta particles, atomic nuclei, atoms and ions. As used herein, particles explicitly include alpha particles, beta particles, positrons, conversion electrons and Auger electrons.

In embodiments, the particle-processing detector is not a particle track detector. In embodiments, the particle-processing detector comprises a semiconductor detector. In embodiments, the semiconductor detector provides an energy resolution equal to or better than 10% of the total energy deposited by the particle in the particle-processing detector. In embodiments, the semiconductor detector provides a position resolution equal to or better than 10 μm. In embodiments, the particle-processing detector comprises a hybrid semiconductor pixelated detector. In embodiments, the particle-processing detector comprises a layer of semiconductor material comprising an active volume and a set of anodes; wherein the set of anodes is provided in electrical contact with a side of the active volume opposite an entrance face of the particle-processing detector. In embodiments, the semiconductor detector has a pixel array size between 8×8 and 1024×1024 pixels. In embodiments, the pixel measures between 1 μm×1 μm and 300 μm×300 μm. In embodiments, the semiconductor detector has a detection area selected over a range of between 10 mm$^2$ to 100 cm$^2$. In embodiments, the semiconductor detector provides a subpixel spatial resolution greater than 750 nm for an equivalent 10 MeV alpha particle. In embodiments, the semiconductor detector is provided proximate to the source of particles.

In an exemplary embodiment, the method comprises a particle-processing detector. In embodiments, the particle processing detector comprises a silicon sensor. In embodiments, the particle-processing detector comprises a scintillation camera. In embodiments, the scintillation camera comprises a scintillation crystal, a PiN diode array, and a light guide, wherein the light guide is a glass spacer. In embodiments, the PiN diode array comprises an array of PiN diodes. In embodiments, the PiN diode array has a pixel array size between 2×2 and 1024×1024 pixels. In embodiments, the scintillation crystal converts alpha particle absorption to light emission. In embodiments, the light guide blurs scintillation light into multiple pixels. In embodiments, the scintillation camera further comprises a charge-coupled device (CCD), or a complementary metal-oxide-semiconductor (CMOS) detector.

In exemplary embodiments, the methods further comprise additional attributes for each particle including at least a portion of: a time, a tissue sample, one or more angles characterizing a direction of travel along the independent particle trajectory at the 2D position.

In embodiments, attributes comprise a set of parameters that are estimated for each particle as an estimated parameter vector and stored as entries in an attribute list, 3D grid of bins or a database. In embodiments, estimation of the set of parameters is performed using a maximum-likelihood algorithm, such as a maximum-likelihood search algorithm. In embodiments, the generating step is performed using a maximum-likelihood algorithm, such as a list-mode maximum-likelihood expectation-maximization algorithm. In embodiments, the attributes comprise a set of parameters that are estimated for each particle as an estimated parameter vector and stored as entries in an attribute list, 3D grid of bins or a database. In embodiments, the estimation of the set of parameters is performed using a maximum-likelihood algorithm. In embodiments, for each particle independently, a point from which the particle emits is constrained to lie within a spherical shell having a thickness that is determined. In embodiments, the thickness is determined by a probability density function that is dependent on a detector energy response. In embodiments, the source of particles can be generated by one or more isotopes. In embodiments, the step of reconstructing the 3D distribution of the source of particles is carried out using an Ordered Subsets-Expectation Maximization (OSEM) algorithm, an Algebraic Reconstruction Technique (ART), or a Simultaneous Iterative Reconstructive Technique (SIRT).

In embodiments, the step of reconstructing the 3D distribution of the source of particles comprises calculating a probability density function for each of a plurality of locations within the source of particles. In embodiments, the probability density function is calculated using one or more computer models from list comprising: a Monte Carlo simulation, an ordered subsets-expectation maximization (OSEM) algorithm, an Algebraic Reconstruction Technique (ART), or a Simultaneous Iterative Reconstructive Technique (SIRT). In embodiments, the probability density function for each location accounts for propagation of particles between that location and the particle-processing detector. In embodiments, the method comprising providing a visual display of the 3D distribution of the source of particles.

In an embodiment, for example, the method further comprises, for at least a portion of the particles, independently measuring an image corresponding to a track of the particle interacting with the particle-processing detector. In an embodiment, for example, the method further comprises, for at least a portion of the particles, determining one or more additional attributes of each of the particles using the image corresponding to the track of the particle. In an embodiment, for example, the one or more additional attributes are selected from the group consisting of a 2D position of a start of the particle track, a direction of travel of a particle at a point along the particle track, and a total energy deposited by a particle along a particle track. In an embodiment, for example, the one or more additional attributes are used to construct the 3D distribution of the source of particles. In an embodiment, for example, the particle-processing detector comprises a track detector.

In another aspect, the present invention provides devices for reconstructing a 3D distribution of a source of particles from within a tissue sample, wherein the particles comprise beta particles, alpha particles, positrons, or conversion electrons. An exemplary device embodiment comprises: a particle-processing detector for detecting the particles; a processor positioned in data communication with the particle-processing detector, wherein the processor is configured for: determining attributes of the particle; wherein the attributes include at least one of: (i) a two dimensional position corresponding to an interaction point where the particle interacts with the particle-processing detector; (ii) an energy that is deposited in the particle-processing detector by the particle; and storing the attributes of the particle; thereby generating attributes for each of the plurality of particles from the source; and reconstructing the 3D distribution of the source of particles using at least a portion of the attributes for each of the plurality of particles. In an embodiment, the device includes a processor for determining both attributes of (i) a two dimensional position corresponding to an interaction point where the particle interacts with the particle-processing detector; (ii) an energy that is deposited in the particle-processing detector by the particle.

In some embodiment, the detector configuration uses a fast camera, such as a camera providing a frame speed capable of generating useful image data. For certain applications, for example, a camera used as a sensor in the present methods and systems is able to acquire frames, for example having a size of 512×512 (or larger), at a frame rate of 35000 frames per second or higher. In some embodiments, for example, estimation of position, energy, and direction of propagation of a particle is achieved with accuracy if the signal (e.g., either light flashes produced by the interaction between a particle and the scintillator, or secondary electrons by the interaction between a particle and the detector itself) corresponding to different particles are spatially well separated in the final detector images. In an ideal case, each image collected by the camera will contain zero or more flashes of light all associated to no more than one particle. If multiple flashes of light corresponding to different particles are present in a detector image, the image data may be exhibit "spatial pileup" (Furenlid, L. R.; Clarkson, E.; Marks, D. G.; Barrett, H. H., "Spatial pileup considerations for pixelated gamma-ray detectors," IEEE Transactions on Nuclear Science, vol. 47, issue 4, pp. 1399-1403, August 2000). Spatial pileup may introduce ambiguities in the way in which flashes of lights are associated to different particles, potentially leading to inaccuracies during the estimation of position, energy and direction of propagation. Fast cameras are advantageous for some applications of the invention because, at high enough frame rates, the probability of spatial pileup is negligible.

In embodiments, the processor comprises a computer, a computer, or other hardware equivalent implementing a computer software. In embodiments, the particle-processing detector comprises a silicon sensor. In embodiments, the device further comprising a tomographic imaging system. In embodiments, the particle-processing detector further comprises a GPU (graphics processing unit), an application-specific integrated circuit (ASIC), or a field-programmable gate array (FPGA). In an embodiment, the particle-processing detector comprises a track detector.

In an exemplary embodiment, the two-dimensional detector comprises a semiconductor detector. In certain embodiments, the semiconductor detector provides an energy resolution equal to or better than 1% of the total energy deposited by the particle in the two-dimensional detector. In certain embodiments, the semiconductor detector provides a position resolution equal to or better than 750 nm. In a specific embodiment, the two-dimensional detector comprises a hybrid semiconductor, pixelated detector. In embodiments, the two-dimensional detector comprises a layer of semiconductor material comprising an active volume and a set of anodes, wherein the set of anodes is provided in electrical contact with a side of the active volume opposite an entrance face of the two-dimensional detector. In embodiments, the semiconductor detector has a 256×256 pixel array. In certain embodiments, the semiconductor detector has a detection area selected over the range of 100 mm$^2$ to 100 cm$^2$. In embodiments, for example, the semiconductor detector provides a subpixel spatial resolution better than 750 nm for equivalent 10 MeV alpha particle. In certain embodiments, the semiconductor detector is provided proximate to the source of particles.

In some embodiments, the step of reconstructing the 3D distribution of the source of particles comprises calculating a probability density function for each of a plurality of locations within the source of particles. In a specific embodiment, for example, the probability density function is calculated using a Monte Carlo simulation. In embodiments, the probability density function for each location accounts for propagation of particles between that location and the two-dimensional detector.

18B provides experimental data of beta particles on a CCD detector without use of a scintillator.

Figure 19:
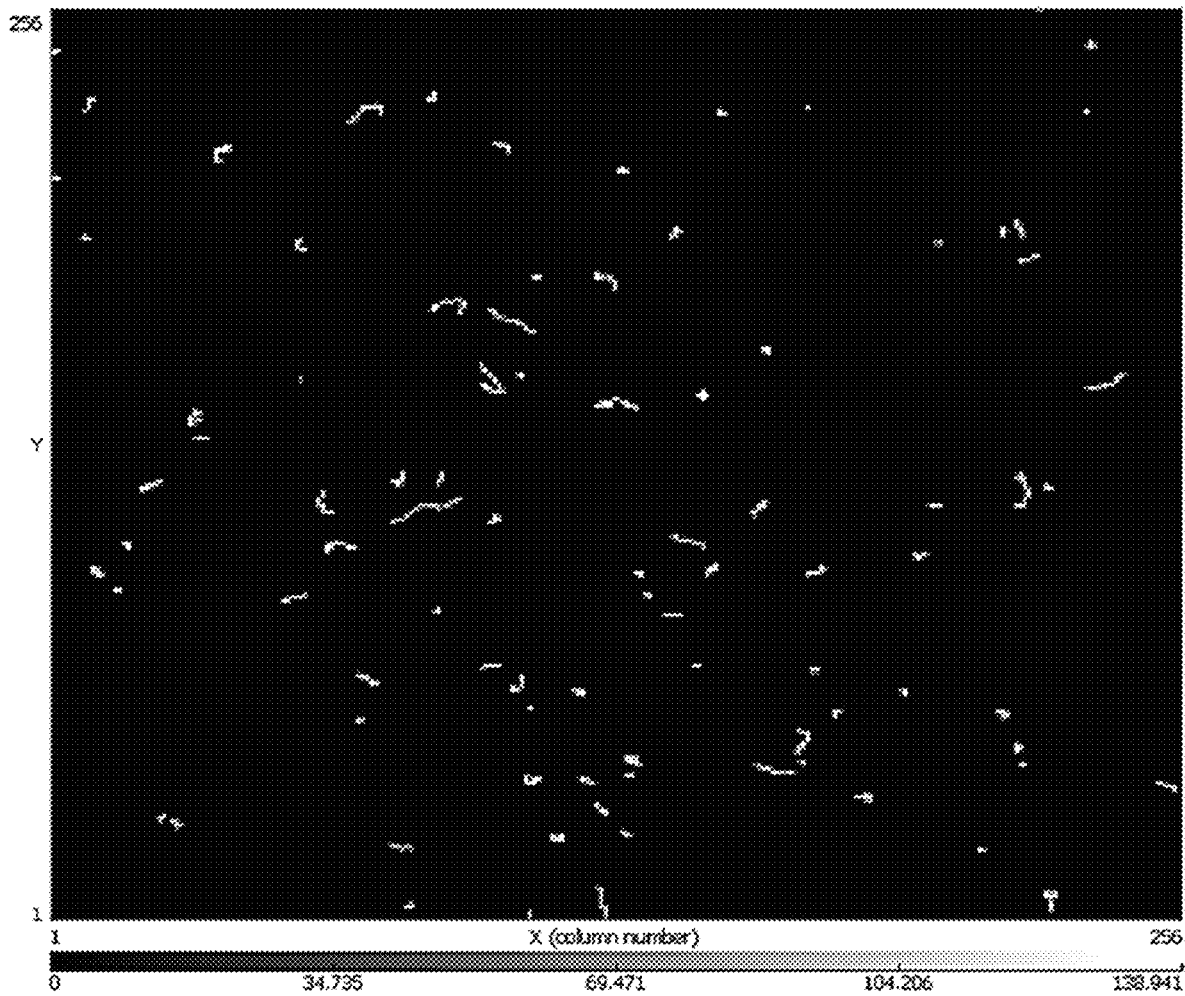

FIG. 19 provides beta particle tracks detected using a WidePIX detector. The tracks can be analyzed and used for reconstruction of the source distribution.

DETAILED DESCRIPTION

In general, the terms and phrases used herein have their art-recognized meaning, which can be found by reference to standard texts, journal references and contexts known to those skilled in the art. The following definitions are provided to clarify their specific use in the context of the invention.

"Particle" refers to an object possessing mass. Particles are distinguished from massless objects, such as photons. Exemplary particles include, but are not limited to, subatomic particles such as protons, neutrons and electrons, high-energy particles such as alpha particles and beta particles, atomic nuclei, atoms and ions. As used herein, particles explicitly include beta particles, positrons, conversion electrons and Auger electrons.

"Alpha particle" refers to a particle comprising two protons and two neutrons. Alpha particles are typically generated by the process of radioactive decay, often referred to specifically as alpha decay. As used herein, alpha particle refers to any particle consisting of two protons and two neutrons, regardless of energy or velocity.

"Two-dimensional detector" and "particle-processing detector" refer to an electronic device capable of measuring attributes, including the energy and the 2-dimensional location of a particle, and other attributes such as direction of a particle or time, at a point of interaction on a two-dimensional surface. Two-dimensional detectors include silicon sensors, and scintillation cameras. Further, a particle-processing detector is one that collects signals from multiple sensors (usually pixels) and uses them to estimate attributes of the particle interaction "Interaction" refers to a process where a particle's kinetic energy is reduced when it is exposed to or otherwise interacts with a material, device or device layer to generate a detectable signal, such as electrons or photons.

"3D position" refers to a unique location within space characterized by three coordinates, such as x, y, and z coordinates. In embodiments a 3D position can be provided by two coordinates (e.g., x and y) located within a plane or within a film or layer of material, and an intensity of the signal at the position provided by the two coordinates.

"2D position" refers to a unique location within plane characterized by two coordinates, such as x and y coordinates.

"Direction" refers to a description of the translation through space of a particle. In embodiments, the direction of travel of a particle is specified by two angles in a spherical coordinate system or by any two components of a unit vector.

"Radiopharmaceutical" refers to a radioactive composition administered to a subject or patient for use in the diagnosis, treatment, cure or prevention of a disease or condition or for use in imaging a tissue or tissue component. In embodiments, a radiopharmaceutical comprises one or more radioisotopes that generate particles upon radioactive decay, such as beta particles. In some embodiments, radiopharmaceuticals generate gamma rays.

"Detectable signal" refers to charged particles, such as electrons, or electromagnetic radiation that can be used for sensing the occurrence of an interaction between a particle and an active material of a position sensitive detector system.

"Semiconductor" refers to any material that is an insulator at very low temperatures, but which has an appreciable electrical conductivity at temperatures of about 300 Kelvin. In the present description, use of the term semiconductor is intended to be consistent with use of this term in the art of microelectronics and electrical devices. Typical semiconductors include element semiconductors, such as silicon or germanium, and compound semiconductors, such as group IV compound semiconductors such as SiC and SiGe, group III-V semiconductors such as AlSb, AlAs, Aln, AIP, BN, GaSb, GaAs, GaN, GaP, InSb, InAs, InN, and InP, group III-V ternary semiconductors alloys such as AlxGa1-xAs, group II-VI semiconductors such as CsSe, CdS, CdTe, ZnO, ZnSe, ZnS, and ZnTe, group I-VII semiconductors CuCI, group IV-VI semiconductors such as PbS, PbTe and SnS, layer-type semiconductors such as $PbI_2$, $MoS_2$ and GaSe, oxide semiconductors such as CuO, $Cu_2O$ and $TiO_2$. The term semiconductor includes intrinsic semiconductors and extrinsic semiconductors that are doped with one or more selected materials, including semiconductor having p-type doping materials (also known as p-type or p-doped semiconductor) and n-type doping materials (also known as n-type or n-doped semiconductor), to provide beneficial electrical properties useful for a given application or device. The term semiconductor includes composite materials comprising a mixture of semiconductors and/or dopants. Impurities of semiconductor materials are atoms, elements, ions and/or molecules other than the semiconductor material(s) themselves or any dopants provided to the semiconductor material. In embodiments, an interaction between a semiconductor and a particle, such as a beta particle, alpha particle, or conversion electron, generates electron-hole pairs within the semiconductor. In embodiments, an interaction between a semiconductor and a particle, such as a beta particle, alpha particle or conversion electron, generates electron-hole pairs that are separated within the depletion region of a semiconductor device.

"List-mode maximum-likelihood expectation-maximization algorithm" or "LMMLEM algorithm" refers to method for image reconstruction. An embodiment of this algorithm is described in L. Parra and H. H. Barrett, "List-mode likelihood—EM algorithm and noise estimation demonstrated on 2D-PET," IEEE Trans. Med. Imag. MI-17:228-235, 1998, which is hereby incorporated by reference.

"Sub-pixel" or "subpixel" are synonymous and refers to a high degree of spatial resolution. In an embodiment of this invention, when the events are recorded with sufficient speed that it is possible to detect the influence of each interaction event on a plurality of detector elements, then one can use multiple pixel signals (from multiple electrodes) for each interaction event to estimate the location of that event to an accuracy that is less than the size of the electrode. It is also possible to estimate attributes other than the location for each interaction event. In some embodiments, depending on the size of the pixel, by fitting the signals to a Gaussian function, a detector provides sub-pixel spatial resolution to about 750 nm for equivalent 10 MeV alpha particles. With bias voltage at 100 V, the energy resolution is about 50 keV FWHM for 5.5 MeV alpha particles.

"Particle track" refers to the path of a particle through an active material, such as a scintillator or a microchannel plate or a deep-depletion CCD device or a deep-depletion CMOS device, along which a detectable signal is generated. A particle track generally begins at the point at which the particle enters the active material. In an embodiment, the particle track optionally ends when the particle exits the material. In an embodiment, the particle track optionally ends when the particle comes to a stop. A "particle track detector" refers to a system for capturing a detectable signal generated as a particle traverses a path through an active material.

"Position dependent signal" refers to a signal generated by detection or measurement of a particle, such as a beta particle, alpha particle or a conversion electron, at a specific point on the trajectory of the particle. In some embodiments, position dependent signals are useful for characterizing the trajectories of particle translating from a source through a detection region. Position dependent signals include optical signals, electronic signals, acoustic signals, magnetic signals, and combinations of these.

"Active material" refers to a device, composition or structure that generates, upon an interaction with a particle, a detectable signal that originates from the specific location within the device, composition or structure that the interaction occurs at.

"Scintillator" "scintillation material" and "phosphor" refers to a composition that emits photons upon an interaction with a particle, such as a beta particle, alpha particle or conversion electron. In embodiments, photons are emitted by these materials upon absorption of a particle. In embodiments, photons are emitted by these materials when these materials interact with a particle and reduce the particle's kinetic energy.

"CCD" or "charge-coupled device" refers to an imaging device used for detection of electromagnetic radiation by generation of and or accumulation of charges upon absorption of electromagnetic radiation. In embodiments, the term CCD refers to a two-dimensional array of CCD elements arranged to obtain an image.

"Deep-depletion CCD" refers to a specific CCD construction where the semiconductor material comprising the active charge generation region or depletion region is thicker than in a conventional CCD device such that it permits detection of absorbed radiation or particles at depths greater than conventional a CCD. "Depletion region" refers to a region of a CCD in which there is a high electric field for the purpose of separating electrons and holes. "CCD well" refers to a region of a CCD or deep-depletion CCD in which charges generated through the absorption of electromagnetic are accumulated.

"CMOS sensor" refers to an imaging device used for detection of electromagnetic radiation. In embodiments, a CMOS sensor is fabricated using conventional methods and technology commonly known in the art of microfabrication and integrated circuit fabrication as "complementary metal-oxide-semiconductor."

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'".

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations that are not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention may be further understood by the following non-limiting examples.

Example 1

Autoradiography Methods

Autoradiography is the use of a radioactive pharmaceutical to study clinical or biological processes. The radiation source is inside the object being studied, and the prefix 'auto' distinguishes it from conventional radiography where an external radiation source is used. Sometimes SPECT (single-photon emission computed tomography) and PET (positron emission tomography) tomography which also use internal radioactive sources, are referred to as in vivo autoradiography, but the term is used much more commonly to refer to ex vivo imaging of a tissue specimen after a biopsy of a patient or in an animal imaging study after the animal is sacrificed.

In these procedures, the radiopharmaceutical is introduced into the living subject, and after a suitable time for it to equilibrate, the specimen is removed and cut with a device called a microtome into very thin slices, often only 5-10 μm thick. Each slice is then placed over a high-resolution imaging detector which is sensitive to charged particles, such as alpha particle, beta particles or Auger electrons, that are emitted by the radioactive isotope used in the pharmaceutical. Depending on the isotope, there may also be x-ray or gamma ray emissions, which can be used for in vivo tomography, but the imaging detectors used in ex vivo autoradiography are designed to be relatively insensitive to these photon emissions.

The resulting 2D autoradiographic slice images can have exquisite spatial resolution, far better than that of SPECT or PET; they can display the details of the radiopharmaceutical distribution at a cellular or subcellular level, but of course only after the specimen is no longer part of a living subject. In principle, the 2D slice images can also be assembled into a 3D image, analogous to those produced by SPECT and PET, but in practice this procedure is both laborious and technically challenging. The technical challenges stem from distortions introduced by the transfer of tissue from the microtome and the imaging detector and/or the tissue dehydration process.

One goal achieved by the present invention is extension of 2D autoradiography to 3D, such that the full volumetric distribution of the pharmaceutical is imaged without having to reassemble the 3D volume from distorted 2D slices.

A second goal achieved by the present invention is obtaining the 3D image with a detector in contact or near contact with just one face of the tissue being imaged, rather than surrounding the tissue with detectors as in SPECT or PET.

A further goal is achieved by the present invention is achieving the two goals with very high spatial resolution, much better than in SPECT or PET, rivaling that of thin-slice autoradiography.

These goals give 3D autoradiography uses for in vivo imaging, not just ex vivo.

An aspect of one embodiment of the invention is the use of charged-particle detectors that provide information about not only the location of the particle when it interacts with the detector but also its direction. With photon detectors, as in SPECT and PET, there is no possibility of learning anything about the direction of the photon from a single interaction with the detector. A high-energy photon travels unimpeded through a detector until it makes a Compton or photoelectric interaction at a single point; in a scintillation detector, each interaction produces a single flash of light. A high-energy charged particle, on the other hand, interacts with the detector all along its path. In a semiconductor detector, the position and energy of each detected alpha particle is measured.

As discussed below, this example describes algorithms to determine the position and direction of an alpha particle at the point it enters the detector. This information is stored about each particle, for example, in a list, 3D (or higher dimensions) grid or other database, and it is used, along with a sophisticated particle transport algorithm, to reconstruct the 3D distribution of the radioactive pharmaceutical.

Major advantages achieved by the embodiments described herein include the ability to produce high-resolution 3D imaging of the distribution of a radioactive pharmaceutical in a tissue without physically slicing it into thin sections. In addition, this technique is applicable to virtually any radioisotope.

3D tomography with a detector on only one side of the tissue can be achieved by the techniques described herein. In addition, the techniques described herein are applicable to living tissue, for example with skin lesions or epithelial lesions accessible with endoscopy. Furthermore, dynamic (4D) studies on living subjects can be achieved.

Example 2

Real-Time Maximum-Likelihood (ML) Methods and Reconstruction Functions

The manuscripts J. Y. Hesterman, L. Caucci, M. A. Kupinski, H. H. Barrett and L. R. Furenlid, "Maximum-likelihood estimation with a contracting-grid search algorithm," IEEE Trans. Nucl. Sci., 57(3), 1077-1084 2010, and A. K. Jha, H. H. Barrett, E. C. Frey, E. Clarkson, L. Caucci, and M. A. Kupinski, "Singular Value Decomposition for photon-processing nuclear imaging systems and applications for reconstruction and computing null functions," Phys. Med. Biol. 60 (2015) 7359-7385 discusses methods and functions and is hereby incorporated by reference.

Example 3

Overview of a Method for Reconstructing 3D Image

Figure 1A:
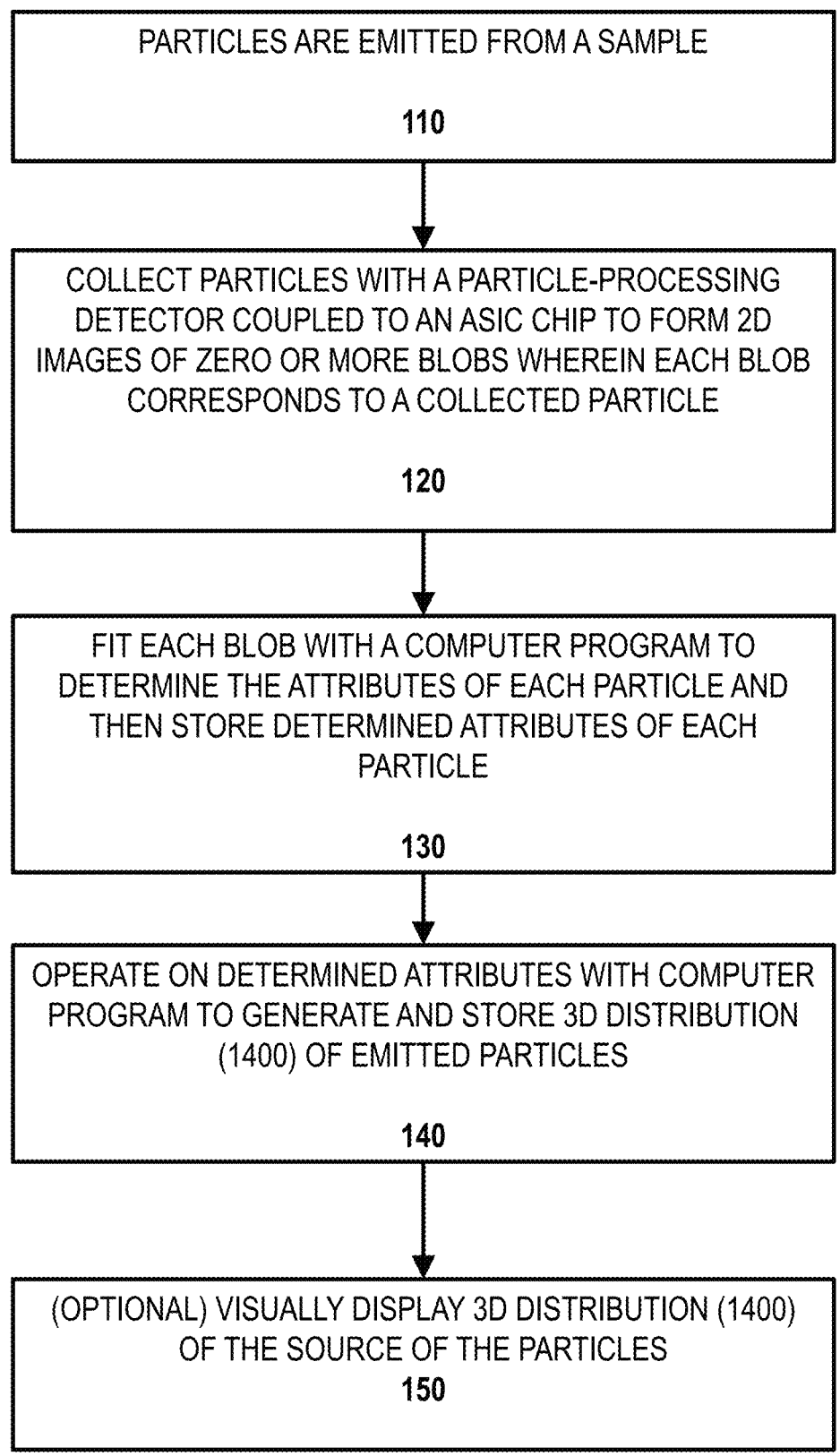
FIG. 1A provides an overview of a method embodiment for determining or reconstructing a 3D distribution of a source of particles within a tissue or object.

FIG. 1A provides an overview of a method embodiment for determining or reconstructing a 3D distribution of a source of particles within a tissue or object. Initially, (110) particles are emitted from a sample. The particles can be beta particles, alpha particles, positrons, or conversion electrons. Next, (120) for a plurality of particles emitted from the sample, the particles are detected by a particle-processing detector in electrical communication with a GPU. The GPU) produces one or more 2D images, in which each image contains zero or more blobs, where each blob corresponds to the data from all pixels that produced signals from one particle interacting in the detector. This process is repeated for each of plurality of particles from the source. Next, (130) each blob is fitted with an appropriate function (such as a Gaussian). This fitting step is carried out by a first computer program that implements a maximum likelihood (ML) algorithm. Determined Attributes of the particles, including at least: a two-dimensional position corresponding to an interaction point where the particle interacts with the particle-processing detector (raw Attributes includes an x position and a y position), and an energy that is deposited in the particle-processing detector characterize the fittings. The Determined Attributes for each particle are stored in in an attribute list, 3D grid of bins or a database. Next, (140) the Determined Attributes (stored in in an attribute list, 3D grid of bins or a database) are operated upon by a second computer program to reconstruct a 3D distribution of the emitted particles. This second computer program performs the reconstruction via the maximum-likelihood expectation-maximization (MLEM) algorithm. Optionally, (150) the 3D reconstruction of the source of the particles can by visually displayed.

As an example, we refer to the process of scanning a frame of data and determining which pixels have contributions from one particle interaction as "frame parsing." Frame parsing indeed produces the blob in the present method, and in may be performed by an ASIC (application-specific integrated circuit), or more commonly a GPU (graphics processing unit) or an FPGA (field-programmable gate array). In some embodiments, GPUs and FPGAs have the advantage of being programmable, while an ASIC is a fixed configuration of electronic gates. To go a step further, the same GPU can be used for real-time attribute estimation for one event, given the data from the pixels within that blob. In some embodiments, the process is ML estimation, however, not simple Gaussian fitting; the key difference is that MLE requires a model for the statistics of the data. A reference describing this approach is Hesterman et al.: J. Y. Hesterman, L. Caucci, M. A. Kupinski, H. H. Barrett and L. R. Furenlid, "Maximum-likelihood estimation with a contracting-grid search algorithm," *IEEE Trans. Nucl. Sci.*, 57(3), 1077-1084 2010. PMC2932457, which is incorporated by reference in its entirety.

Figure 1B:
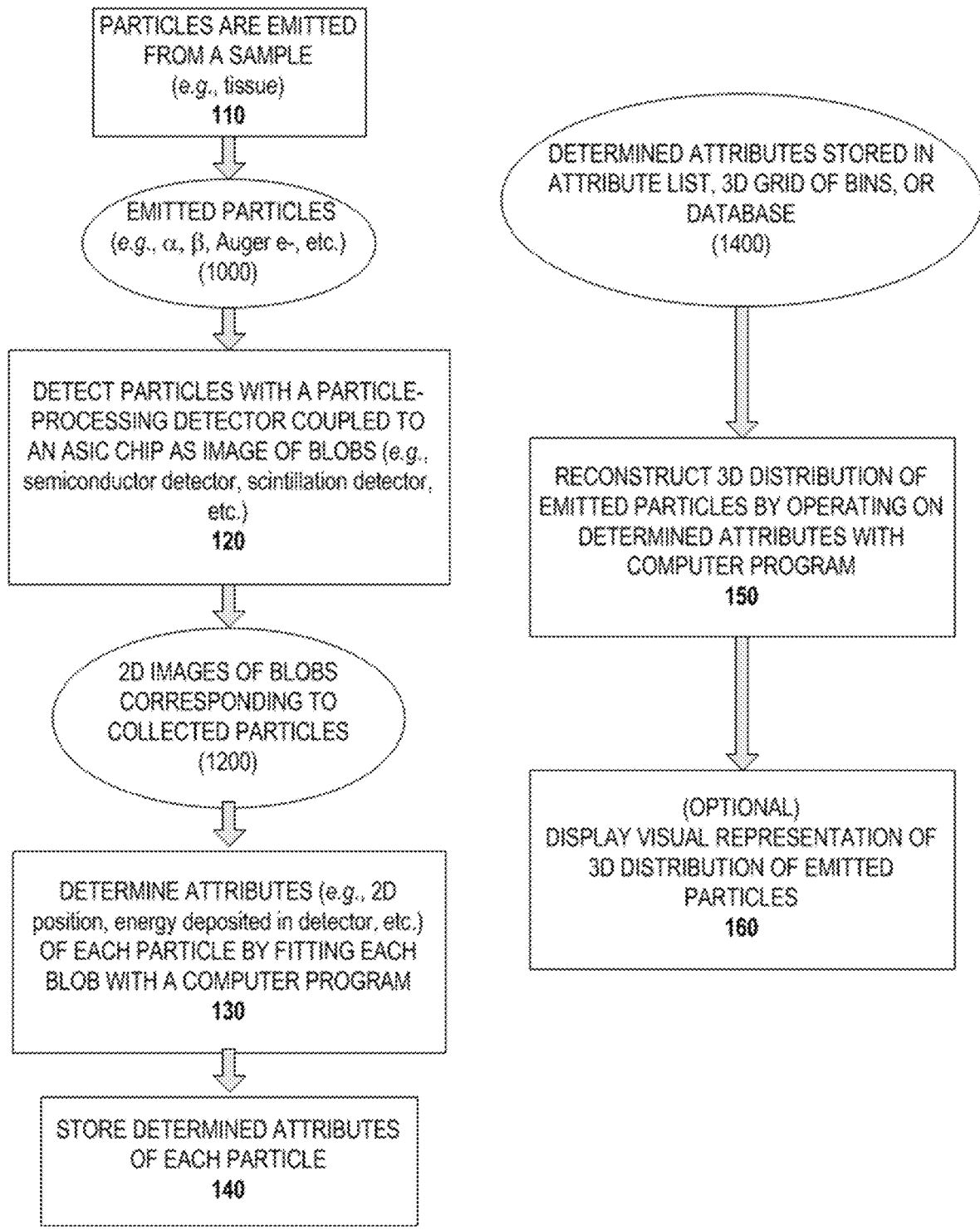
FIG. 1B provides an overview of a method embodiment for determining or reconstructing a 3D distribution of a source of particles within a tissue or object.

FIG. 1B provides an overview of a method for determining or reconstructing a 3D distribution of a source of particles within a tissue or object includes the following. Initially, (110) autoradiography particles (1000) are emitted from the source of charged particles randomly with the time between the emission of one particle and the next particle occurring according a known probability density function. The probability density function of the emission of charged particles is well known to those skilled in the art. Next, (120) the emitted particles are detected and imaged (1200) by the particle-processing detector for a period of time. The imaging initiates at a time T1 and continues until imaging concludes at a time T2. During this time interval, N images (1200) are collected by the detector. Some particles are detected by the detector and they will produce blobs in the images (1200). Some images (1200) might have blobs while some other images (1200) might have no blobs. Each detected particle will produce one blob in one of the N images (1200). Next, (130) each blob is fitted with an appropriate function (such as a Gaussian). This fitting step is carried out by a first computer program that implements a maximum likelihood (ML) algorithm. The fittings are characterized by Determined Attributes of the particles, including at least: a two-dimensional position (raw Attributes includes an x position and a y position), and an energy. Next (140) the Determined Attributes for each particle are stored in an attribute list, 3D grid of bins or a database (1400). Next, (150) the Determined Attributes (stored in in an attribute list, 3D grid of bins or a database) are operated upon by a second computer program to reconstruct a 3D distribution of the emitted particles. This second computer program performs the reconstruction via the maximum-likelihood expectation-maximization (MLEM) algorithm. Optionally, (160) the 3D reconstruction of the source of the particles can by visually displayed.

Example 4

Alpha-Particle Emission Tomography (αET)

Targeted alpha-particle therapy has advantages over beta-particle therapy for treatment of malignant disease. The range of alpha particles in tissue is short, with little radiation dose to surrounding non-target tissues, and the linear energy transfer is high, resulting in cytotoxicity for the target tissue. Targeted alpha imaging and therapy are promising for localizing and eliminating minimal residual disease and micrometastases, which if not ablated will lead to tumor relapse.

Because alpha particles lose energy approximately in proportion to the amount of tissue they traverse, the energy deposited in the detector by an alpha particle allows quantification of the path length the alpha particle traveled in the tissue. In an embodiment, the particle's energy is deposited on the detector, along with the position of interaction of the particle with the detector's entrance face to introduce new imaging methods and reconstruction algorithms applicable to alpha-particle therapy and imaging.

System Description

In an embodiment, semiconductor detectors that measure position as well as energy of each detected alpha particle are used. In addition to position, energy provides depth information about the object, thus making a 3D reconstruction of the object feasible.

Figure 2:
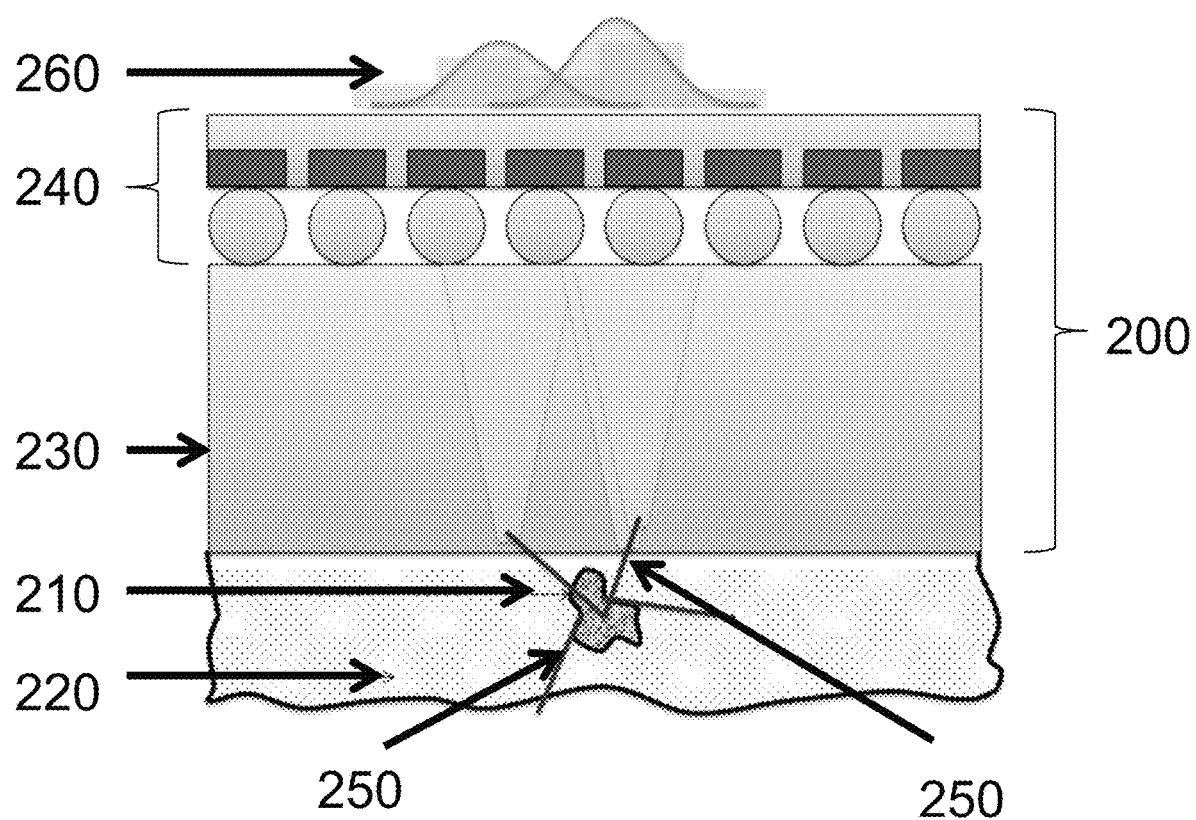
FIG. 2 illustrates an exemplary embodiment of a system for determining the 3D reconstruction of a particle-generating object located within a tissue.

FIG. 2 illustrates an exemplary embodiment of a system 200 for determining the 3D reconstruction of a particle-generating object 210 located within a tissue (220). System 200 comprises a 300 μm silicon sensor 230 and a readout GPU (graphics processing unit) 240. Particles generated by the particle-generating object travel along paths 250 through the tissue 220, where they optionally undergo absorption and scattering. When the particles reach the silicon sensor 230, interactions along paths 250 between the particles and the sensor 230 generate electromagnetic radiation which is collected by the GPU chip In an embodiment of the invention, the imaging system includes a hybrid semiconductor pixelated detector to directly sense alpha particles. One possible detector configuration includes a layer of semiconductor material (which we will refer to as the "detector's active volume"), a set of anodes placed on one side of the detector's active volume, and some data-processing circuitry (such as a GPU (graphics processing unit)) that acquires the anodes signals and convert them into pixel counts (or any other suitable data format). Although not limited to the case of the aforedescribed detector, an embodiment of the setup shown in FIG. 2.

A requirement for the detector is that it must provide accurate 2D position information as well as good energy resolution. The sample tissue being imaged is placed in contact or in close proximity to the detector's active volume face opposite to the anodes, as shown in FIG. 2. Geometric parameters of the detector (such as the material making up the detector's active volume, thickness and surface area of the active volume, bias voltage—if any—applied across the detector's active volume, number of anodes and their spacing/arrangement, data format for the detector output, etc.) are design parameters of the detector. These design parameters, which will affect the statistics of the data in a complicated way, are assumed known and will be supplied to the data reconstruction algorithm (or any other computer code that processes detector data).

Alpha particles emitted upon radioactive decay occurring in the tissue to be imaged will typically travel no more than 10 μm within the detector's active volume. Upon interaction of an alpha particle inside the detector's active volume, the alpha particle's residual energy will yield a shower of electron-hole pairs inside the detector's active volume. The number of electron-hole pairs generated is proportional to the particle's residual energy. The bias voltage applied across the detector's active volume forces the electrons towards the anodes, where they get collected. This process induces a current in each anode that is proportional to the number of electrons reaching the anode. Currents generated at the anodes are measured and converted to computer-readable data by the detector. Thus, in a cascading effect, alpha particles emitted within the tissue sample produce data that are acquired and processed by a computer.

Figure 3A:
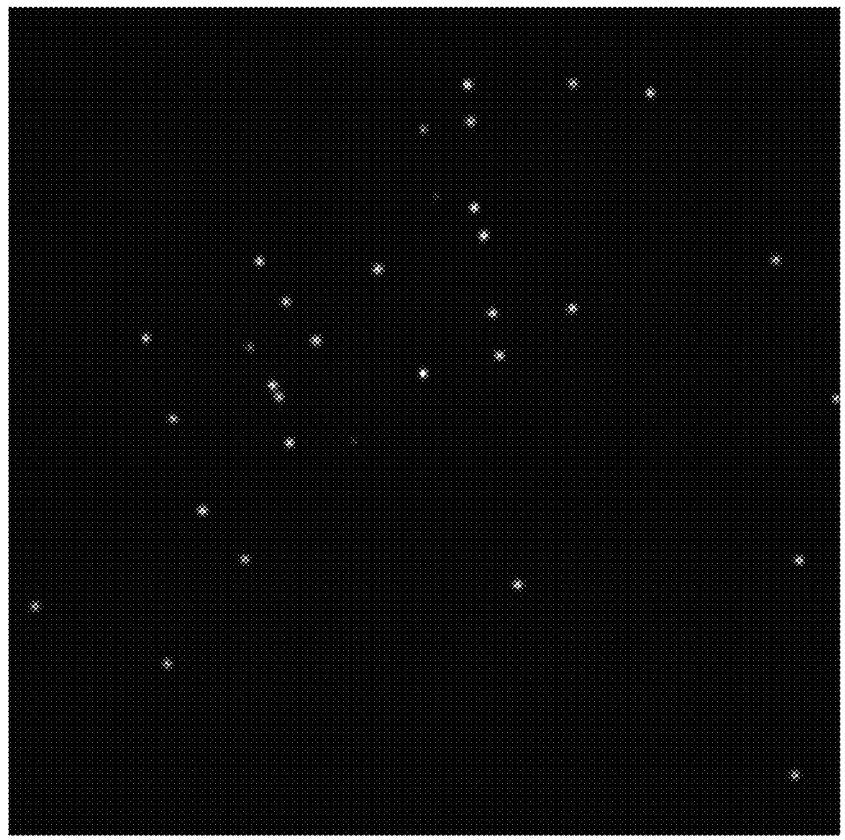
FIG. 3A provides an exemplary 2D image associated with a multitude of alpha particle interaction events (i.e., detections) with the detector.
Figure 3B:
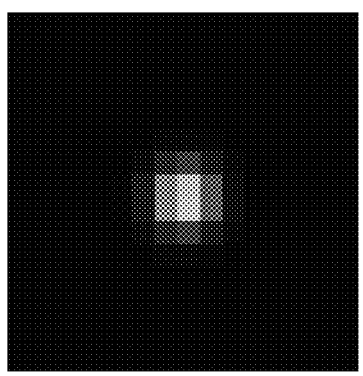
FIG. 3B, provides blowup of a blob shown in FIG. 3A.
Figure 3C:
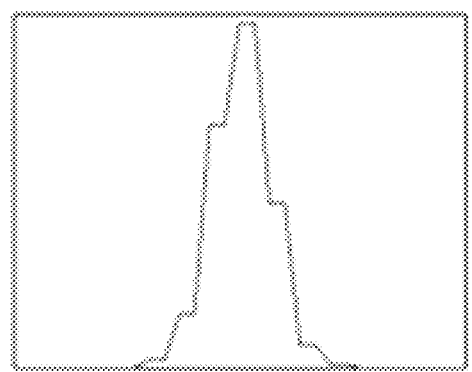
FIG. 3C provides a profile of the blob shown in FIG. 3B

An exemplary 2D image is shown in FIG. 3A, and can be associated to a multitude of alpha particle interactions (i.e., detection) with the detector. For each "blob" shown in FIG. 3A, a 2D position can be calculated and related to the 2D location at which the alpha particle entered the detector's active volume. Furthermore, the sum of the pixel intensities associated to any given blob is proportional to the particle's residual energy. The proportionality constant can be calculated from the detector properties (such as material, bias voltage, etc.). A blowup of a blob shown in FIG. 3A is presented in FIG. 3B, and a profile of the blob shown in FIG. 3B is presented in FIG. 3C.

Besides 2D position and particle residual energy, other quantities (such as time and direction of travel) can be estimated as well. In an embodiment, the set of parameters estimated for each particle is identified as the "estimated parameter vector." The estimated parameter vector of each alpha particle is stored in a list, and this list is used to reconstruct the 3D distribution of the radioactive pharmaceutical. This data arrangement is referred to as "list-mode."

Data Processing and Reconstruction

Because the alpha particle's initial energy (i.e., the energy of the particle emitted upon radioactive decay) is known, knowledge of the particle's residual energy as it enters the detector face allows calculation of the energy the particle lost while traveling within the tissue. In turn, from the amount of energy lost by the particle, the total distance the particle traveled within the tissue can be calculated.

Figure 4:
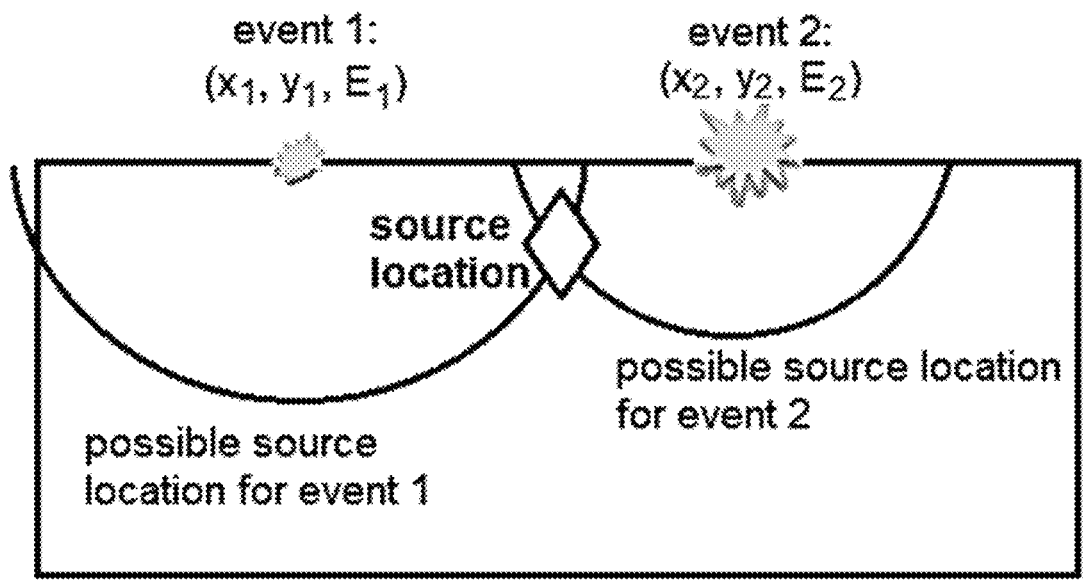
FIG. 4 illustrates a simplified case of two alpha particles emitted by a point-like radioactive source inside the tissue sample.

As shown in FIG. 4, the 2D location at which the particle enters the detector and the distance the particle has traveled in the tissue define a spherical shell in object space (i.e., the tissue). The model constrains the point at which the alpha particle was emitted to lay on this spherical shell. In the simplified case of all alpha particles emitted from a point-like region in the tissue, the spherical shells will all intersect at the emission point.

FIG. 4 shows simplified case of two alpha particles emitted by a point-like radioactive source inside the tissue sample. The 2D location of interaction for the first alpha particle is $(x_1, y_1)$ and the particle's residual energy is $E_1$. The 2D location of interaction for the second alpha particle is $(x_2, y_2)$ and the particle's residual energy is $E_2$. In our example, $E_1 < E_2$, which implies that the first particle has traveled inside the tissue a longer distance than the second particle has (the different size of the sparkles located at $(x_1, y_1)$ and $(x_2, y_2)$ has been chosen to reflect the fact that $E_1 < E_2$. The two spherical shells that denote the possible source locations for each particle intersect at the location of the point-like radioactive source.

Given a list of estimated parameter vectors, a method of image reconstruction for this problem is the list-mode maximum-likelihood expectation-maximization (LMMLEM) algorithm. For the purpose of discussing the reconstructing algorithm and simulation results, it will be assumed that each estimated parameter vector contains estimates $(\hat{x}, \hat{y})$ of the 2D location of interaction on the detector's face, as well as an estimate $\hat{E}$ of the particle's energy as it enters the detector.

Figure 5:
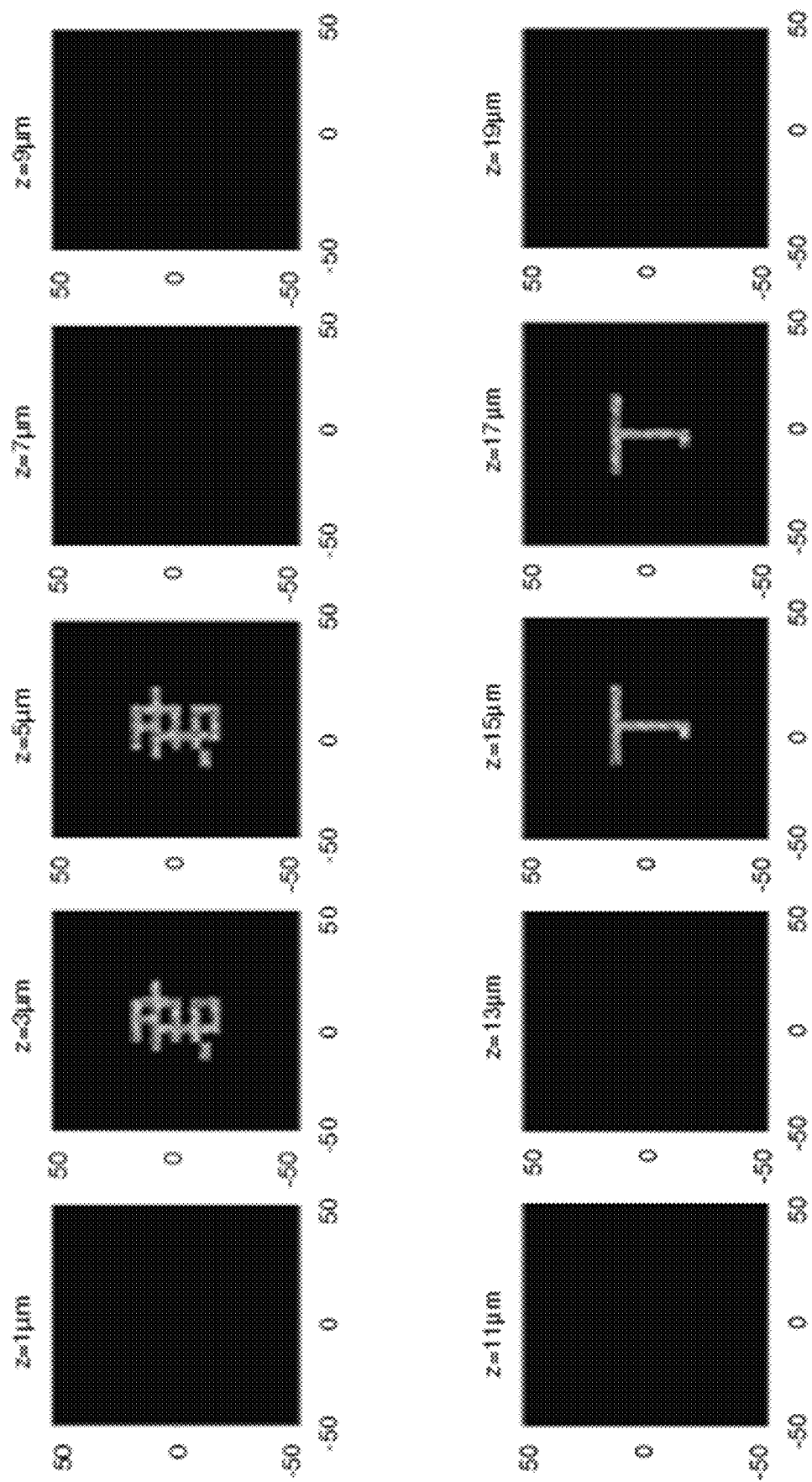
FIG. 5 provides an actual alpha particle emission pattern in sliced view.
Figure 6:
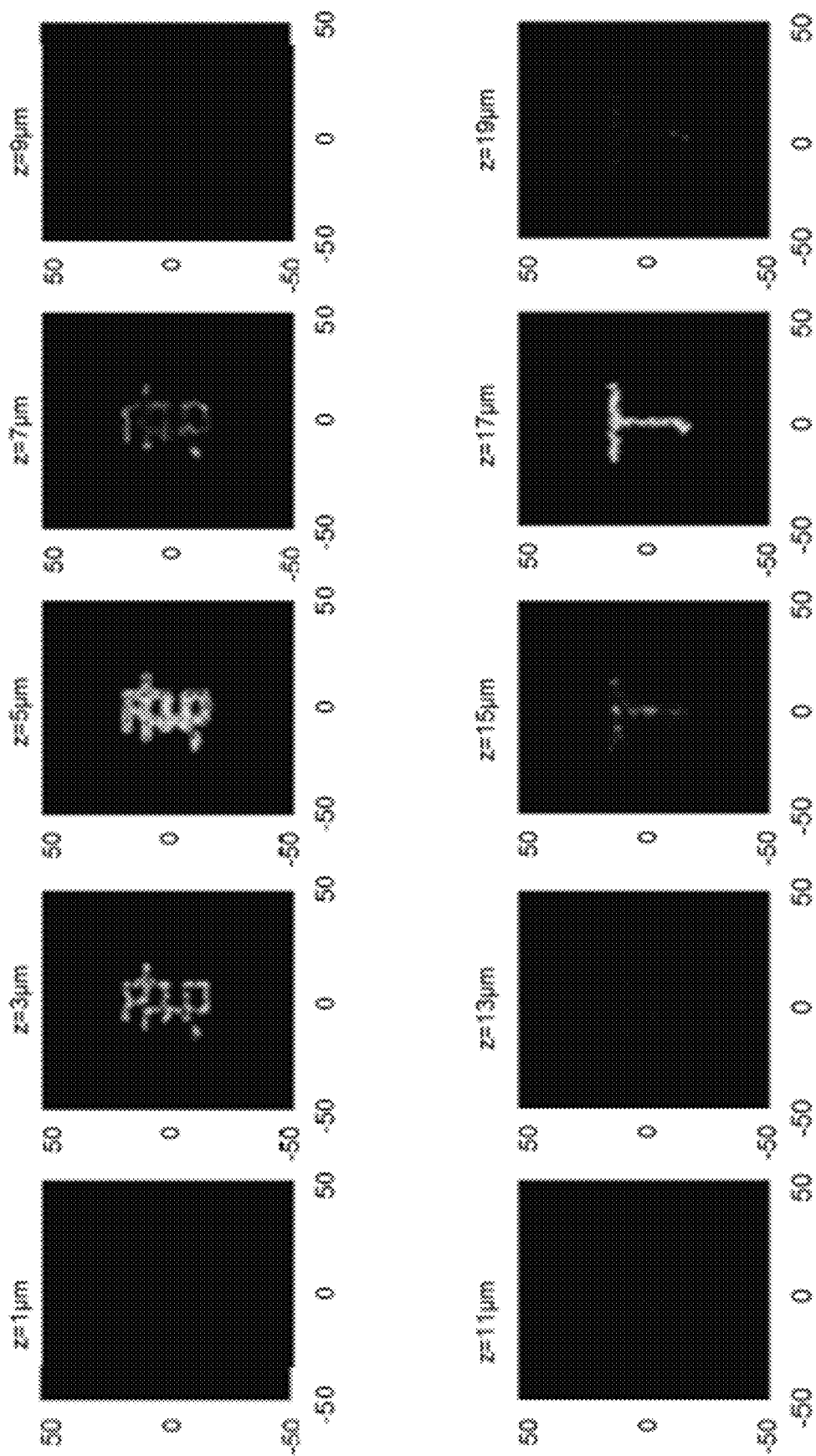
FIG. 6 provides the reconstructed 3D distribution of the object shown in FIG. 5.

A preliminary study indicated that alpha-particle emission tomography (αET) reconstruction can achieve a resolution of 1-2 μm or better across a relatively large field of view. In the simulation study, position resolution of the detector is assumed to be 750 nm, and the energy resolution to be 1% of the total energy deposited. FIG. 5 shows the actual alpha particle emission pattern in sliced view and the reconstructed 3D object is shown in FIG. 6.

Figure 7:
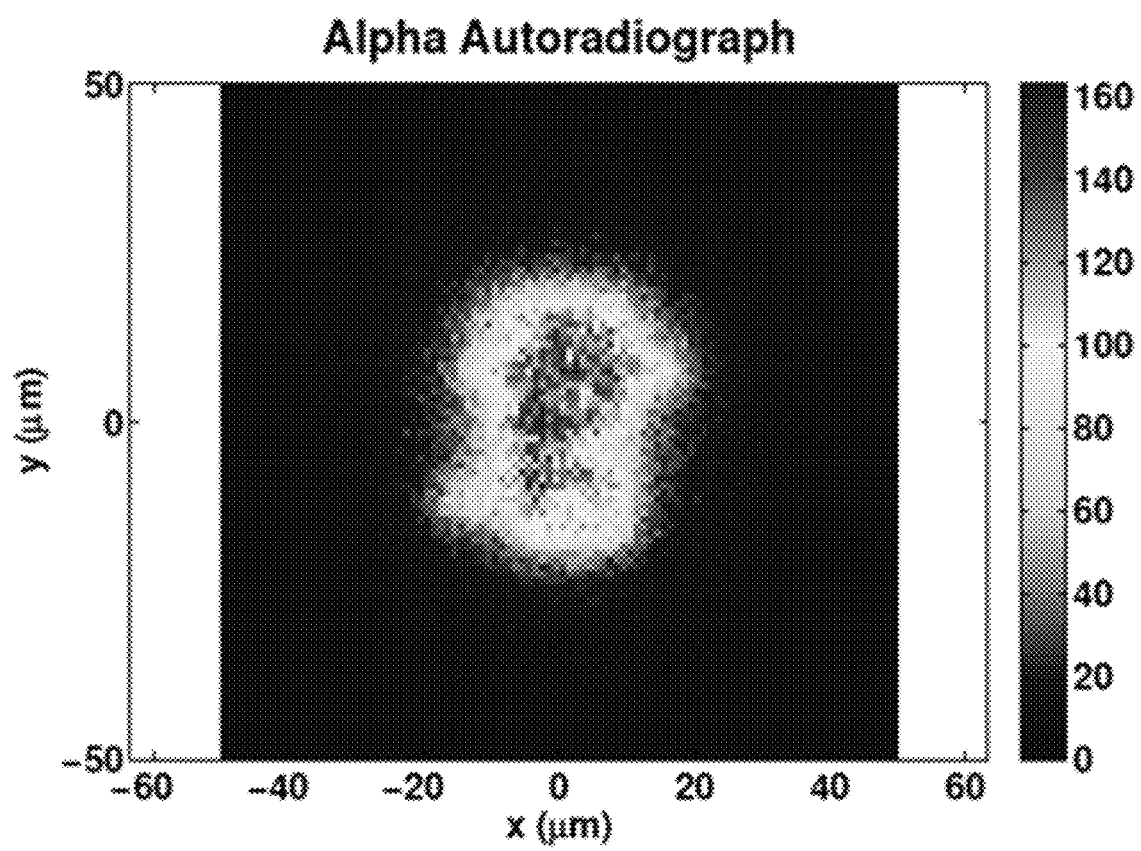
FIG. 7 provides a conventional alpha autoradiograph of the same object is shown in FIG. 5.

As a comparison, a conventional alpha autoradiograph of the same object is shown in FIG. 7.

Example 5

An Embodiment of an αET System

Introduction

Alpha particles have desirable properties for radionuclide therapy, including localized deposition of energy with sparing of nearby tissues, provided that the alpha particles are guided specifically to their target. Antibodies to tumor antigens as well as peptides targeting tumor cell-surface receptors can provide this specific targeting. Studies of antibodies labeled with alpha emitters such as $^{211}$At, $^{213}$Bi and $^{225}$Ac for cancer treatment are currently in progress.

Accurate radiation dose estimation for alpha emitters requires knowledge of not only whole-body biodistribution but also cellular-level distribution of the alpha particles. Knowledge of cellular distribution within the tumor will enable prediction of the radiation dose to the tumor, and knowledge of localization during excretion, such as the specific cellular localization in the kidneys, will predict whether toxic effects will result.

When alpha emissions are accompanied by gamma or x-ray photons, standard imaging methods can be used, but the usual limitations on spatial resolution will apply. When no photons are present, direct alpha imaging is required.

The distinctive physical properties of alpha particles enable αET. Unlike beta particles, alpha particles have discrete energy spectra, with highly monoenergetic emission lines associated with particular nuclear transitions. In low-atomic-number materials such as water or tissue, alpha particles interact with matter primarily through Coulomb forces between their positive charges and the negative charges of the orbital electrons within the absorber atoms. At any given time, the particle is interacting with many electrons, so the net effect is to decrease its velocity continuously until the particle is stopped. Except at their very end, the tracks tend to be quite straight because the particle is not significantly deflected by any one encounter, and interactions are statistically uniform in all directions. The distance an alpha particle travelled is therefore characterized by the energy deposited in a given absorber material [1]. Hence, the path length is a function of the particle residual energy. When an alpha particle emitted in a homogeneous medium is detected at location (x, y) with energy E, the source is restricted to a spherical shell centered at (x, y) with radius determined by E, as illustrated in FIG. 4.

FIG. 4 provides an illustration of an αET system with an energy-sensitive imaging detector. Alpha particles emitted within the tissue propagate along straight lines. From each measured position ($\hat{x}_d$, $\hat{y}_d$) and energy $\hat{E}$ of an alpha particle leaving the tissue, one can localize the emission event to a spherical shell. A 3D reconstruction can be achieved from a list of detected events.

System Configuration

An exemplary αET imaging system includes a hybrid semiconductor pixel detector to directly sense alpha particles. A requirement for the detector is that it provides accurate position information as well as good energy resolution. Semiconductor detectors allow for good energy resolution because the average energy necessary to create an electron-hole pair is smaller than that needed for other types of charged particle detectors. An embodiment is illustrated in FIG. 2: The detector is placed in contact or in close proximity with a sample tissue. Alpha particles emitted by a radioactive isotope inside the tissue are detected by the silicon sensor and produce measurable signals in the detector.

Figure 8:
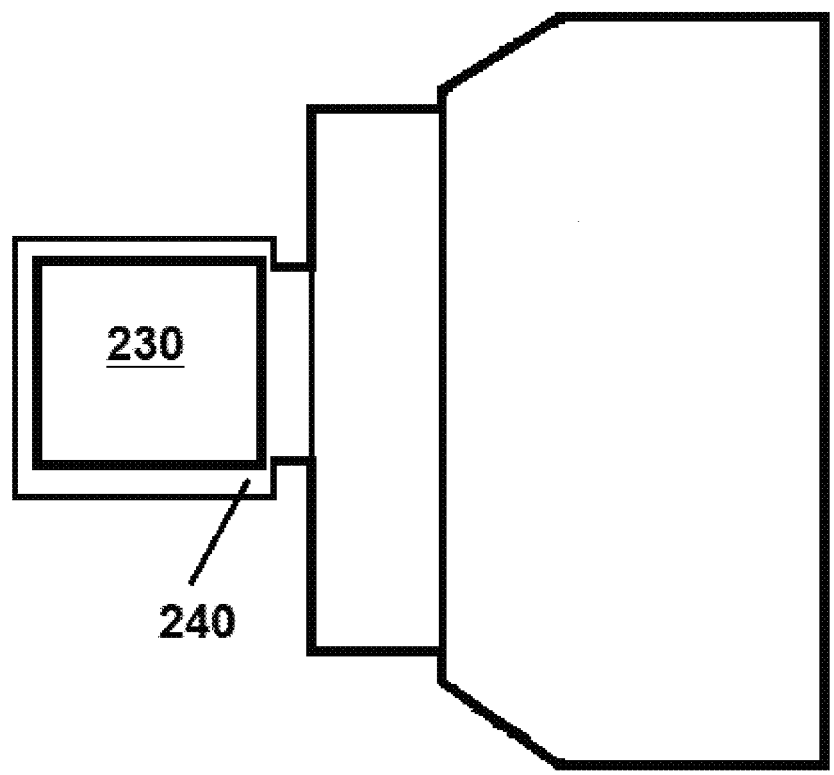
FIG. 8 provides a photograph of one embodiment of a particle-processing detector.

FIG. 8 provides a photograph of one embodiment of a particle-processing detector. The hybrid semiconductor pixel detector (ModPIX; WidePIX company) in the system has 256×256 pixels, each 55 μm×55 μm. The detecting area of the silicon sensor is about 14 mm×14 mm. The large number of electron-hole pairs produced upon interaction of an alpha particle with the detector material gives rise to pixel intensities that approximate a 2D Gaussian function. By fitting the signals to a Gaussian function, the detector provides sub-pixel spatial resolution to about 750 nm for equivalent 10 MeV alpha particles [2]. With bias voltage at 100 V, the energy resolution is about 50 keV FWHM for 5.5 MeV alpha particles [3].

Forward Model

A continuous-to-continuous model of an αET system with kernel $h(x_d, y_d, E; x, y, z)$ that maps an object $f(x, y, z)$ into estimated data $g(x_d, y_d, E)$ can be described as [4]:

$$g(\hat{r}_d) = \int_{V_f} d^3 R \int_{S_d} dx_d dy_d \int_0^\infty dE h(r_d; R) pr(\hat{r}_d|r_d) f(R), \quad (1)$$

where $V_f$ is the object space; $S_d$ is the detector surface; $\hat{r}_d$ denotes estimated attributes ($\hat{x}_d$, $\hat{y}_d$, $\hat{E}$) and $f(R) = f(x, y, z)$ refers to the density of the alpha radioactive tracer, measured in $1/mm^3$. The function on the left-hand side of this equation $g(\hat{r}_d)$, is the density of detected alpha particles that pass through tissue and enter the detector at estimated position ($\hat{x}_d$, $\hat{y}_d$) with estimated energy $\hat{E}$; the units of $g(\hat{r}_d)$ are $1/(\mu m^2 \cdot MeV)$. The factor $pr(\hat{r}_d|r_d)$ characterizes the ability of the detector and electronics to perform the estimation. The kernel $h(r_d; R)$ is the ideal response of the system at $r_d$ to a delta function of activity at point R in object space. Alpha particles travel through tissue in a nearly straight path with energy decreasing continuously. The energy E of an alpha particle as a function of the distance $\ell$ the particle traveled has been described by aStar [5]. This allows us to use the estimated detection location ($\hat{x}_d$, $\hat{y}_d$) and the estimated alpha particle energy $\hat{E}$ to restrict the origin of the alpha particle to the vicinity of a spherical shell centered at ($\hat{x}_d$, $\hat{y}_d$). For αET, the kernel in equation (1) is:

$$h(x_d, y_d, E; x, y, z) = \frac{z}{4\pi \ell^3} \delta(E - E(\ell)) \quad (2)$$

where $\ell = \sqrt{(x_d - x)^2 + (y_d - y)^2 + z^2}$ is the distance from the emission point of an alpha particle to the position where it was detected. We assumed the detector is located at z=0. The sensitivity, which is the probability of a decay at position (x, y, z) being detected, is given by $$s(x, y, z) = \frac{1}{2}\left(1 - \frac{z}{\ell_0}\right), (z \leq \ell_0), \quad (3)$$

where $\ell_0$ is the range of an alpha particle in a given material, which is related with alpha decay energy of the source. For a 5.2445 MeV alpha particle ($^{239}$Pu), $\ell_0$ is approximately 40 μm in soft tissue.

If maximum-likelihood methods are used to estimate $\hat{r}$ from pixel intensities, then the probability density function $pr(\hat{r}|r)$, which describes how well r is estimated from the detector outputs, asymptotically approximates a multivariate normal PDF with mean r [6]. In addition, by taking advantage of translational symmetry, the detector response is shift invariant in areas excluding detector boundaries. Therefore, $pr(\hat{r}_j|n)$, the probability of measuring $\hat{r}_j = (\hat{x}_j, \hat{y}_j, \hat{E}_j)$ when a particle is emitted from voxel n, is approximated as $$pr(\hat{r}_j, \hat{E}_j | n) = \quad (4)$$
$$pr(0, 0, \hat{E}_j | m) \approx \left.\frac{d\ell}{dE}\right|_{\hat{E}_j} \frac{1}{V} \int\int\int_{V_m} \frac{z}{4\pi R^3} G(R; \hat{\ell}_j; \sigma_j) d^3 R,$$

where V is voxel volume and the m-th voxel, $V_m$, corresponds to $V_n$ after shifting $r_j$ to the origin. $G(R; \hat{\ell}_j, \sigma_j)$ is a one-dimensional Gaussian function with mean $\hat{\ell}_j$ and standard deviation $\sigma_j$ both depending on $\hat{E}_j$.

Reconstruction with Expectation Maximization Algorithm

The Expectation Maximization (EM) algorithm is an iterative algorithm to solve inverse problem. The list-mode EM algorithm takes the form [6]:

$$\hat{f}_n^{(k+1)} = \hat{f}_n^{(k)} \left\{ \frac{1}{VS_n} \sum_{j=1}^{J} \frac{pr(\hat{r}_j | n)}{\sum_{n'=1}^{N} pr(\hat{r}_j | n') \hat{f}_{n'}^{(k)}} \right\} \quad (5)$$

Figure 9A:
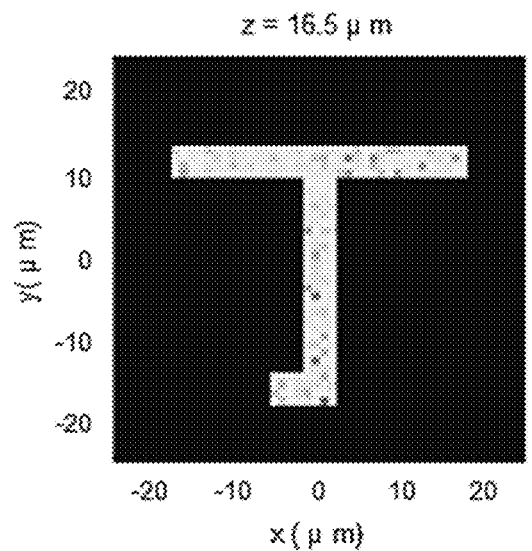
FIG. 9A shows an image of a true decay pattern of one slice located at z=5.5 μm.
Figure 9B:
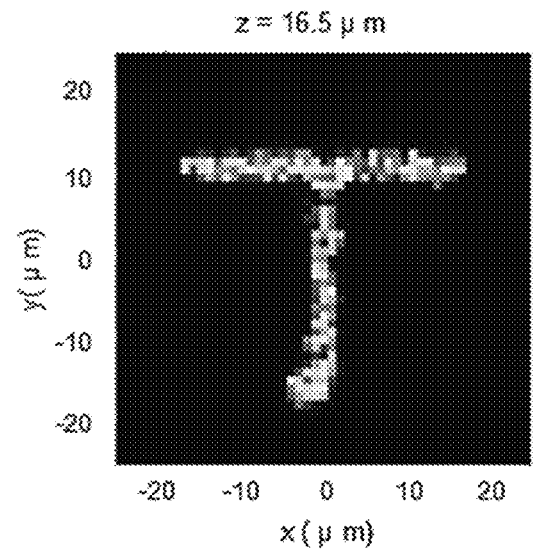
FIG. 9B shows an image of the same object of FIG. 9A reconstructed from 10$^6$ events of one slice located at z=5.5 μm.
Figure 9C:
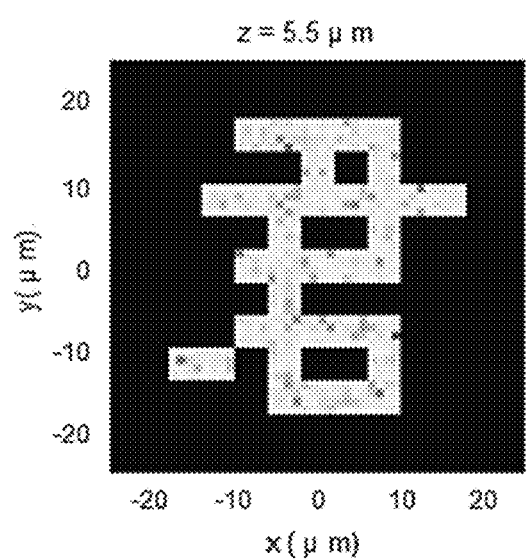
FIG. 9C shows an image of a true decay pattern of one slice located at z=16.5 μm.
Figure 9D:
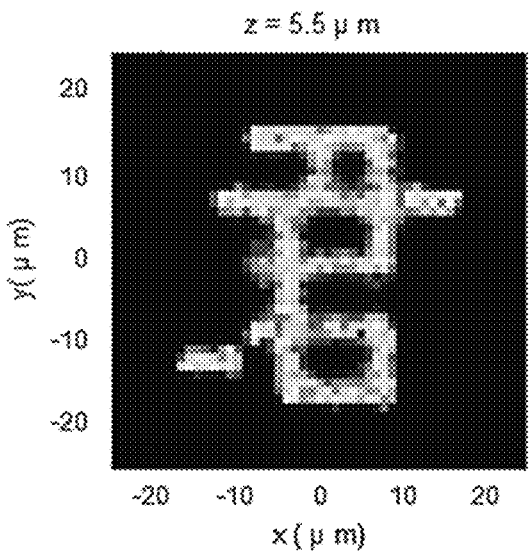
FIG. 9D shows an image of the same object of FIG. 9C reconstructed from 10$^6$ events of one slice located at z=16.5 μm

A slab of 1 mm×1 mm×50 μm tissue with 1 μm³ cubic voxels is discretized. Assuming position standard deviation equals to 320 nm, and energy resolution 1% of the energy detected, Geant4-simulated data are reconstructed according to equation (5). FIG. 9 shows the central part of slices of a reconstructed 3-D object compared with the true decay pattern. The true decay pattern is contrasted with an object reconstructed from $10^6$ events. The object consists of two layers, located at z=6 μm and z=16 μm, each 4 μm thick. FIG. 9A shows an image of a true decay pattern of one slice located at z=5.5 μm. FIG. 9B shows an image of the same object reconstructed from $10^6$ events of one slice located at z=5.5 μm. Similarly, FIG. 9C shows an image of a true decay pattern of one slice located at z=16.5 μm, while FIG. 9D shows an image of the same object reconstructed from $10^6$ events of one slice located at z=16.5 μm. Each slice is 1 μm thick.

For comparison, a conventional alpha autoradiograph is shown in FIG. 7 of the same simulated object in FIG. 9. The information of the object located deeper in the tissue is buried by the strong signal from shallower object.

Alpha Emission Tomography (αET) is an imaging modality that produces a three-dimensional image of the distribution of alpha-particle-emitting radioisotope sources. A system configuration and a mathematical forward model are described. An Expectation Maximization reconstruction algorithm is introduced. The simulation results show that in addition to position, energy information makes a three-dimensional reconstruction of an alpha radioactive distribution possible. In simulations, the resolution of the system is on the scale of 1 μm. Alpha Emission Tomography has the potential to achieve imaging of sample tissue with subcellular resolution. In real experiments, the detector response varies from pixel to pixel

REFERENCES

[1] G. F. Knoll, Radiation detection and measurement. Wiley, 2010.
[2] J. Jakubek, A. Cejnarova, T. Holy, S. Pospisil, J. Uher, and Z. Vykydal, "Pixel detectors for imaging with heavy charged particles," Nucl. Instr. and Meth. A, 2008.
[3] C. Granja, P. Krist, D. Chvatil, J. Solc, S. Pospisil, J. Jakubek, and L. Opalka, "Energy loss and online directional track visualization of fast electrons with the pixel detector timepix," Radiation Measurements, 2013.
[4] H. H. Barrett and K. J. Myers, Foundations of image science, Wiley, New York, 2004.
[5] M. J. Berger, J. Coursey, M. Zucker, and J. Chang, Stopping-power and range tables for electrons, protons, and helium ions. NIST Physics Laboratory, 1998.
[6] L. Caucci, L. Furenlid, and H. Barrett, "Maximum likelihood event estimation and list-mode image reconstruction on GPU hardware," in Nuclear Science Symposium Conference Record (NSS/MIC), 2009 IEEE, 2009.

Example 6

Physics

Figure 10A:
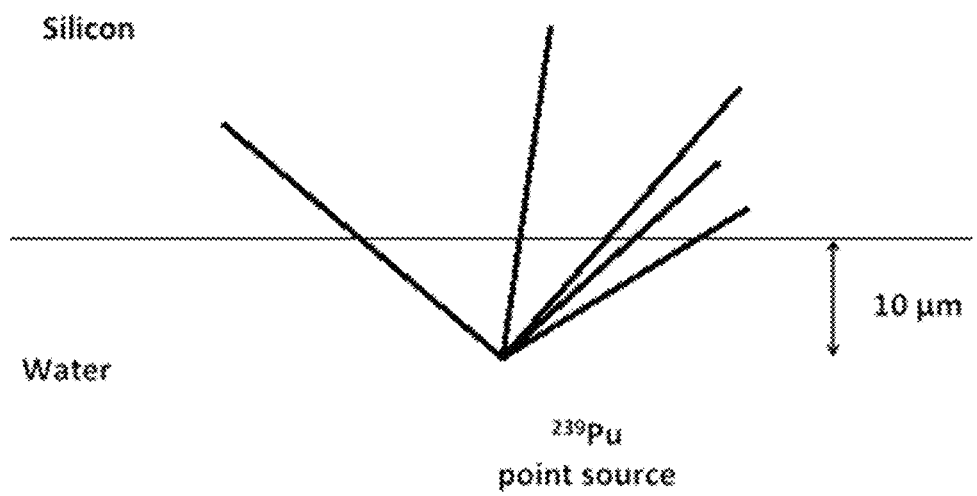
FIG. 10A shows Geant4-simulated tracks of $^{239}$PU alpha particles in water.
Figure 10B:
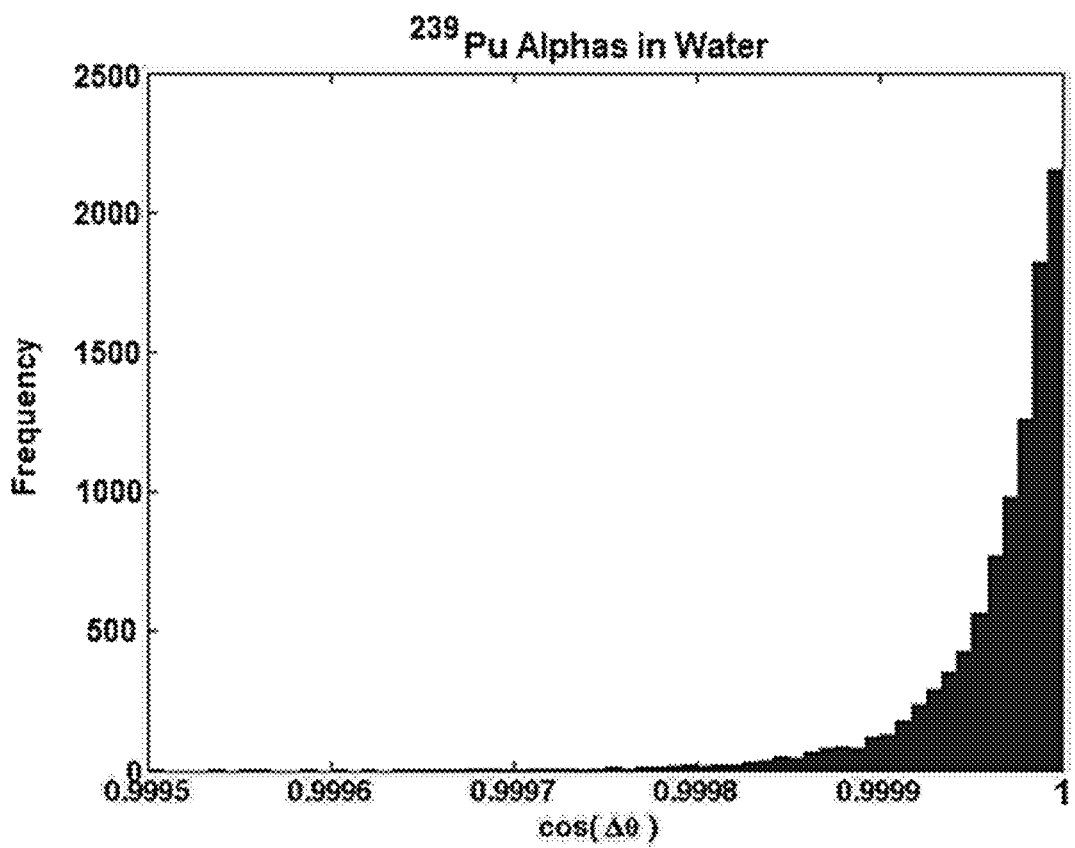
FIG. 10B shows the distribution of the angular deviation Δθ from straight line propagation. The angular deviation of Geant4 simulated data has mean 1.00° and standard deviation 0.28°.
Figure 10C:
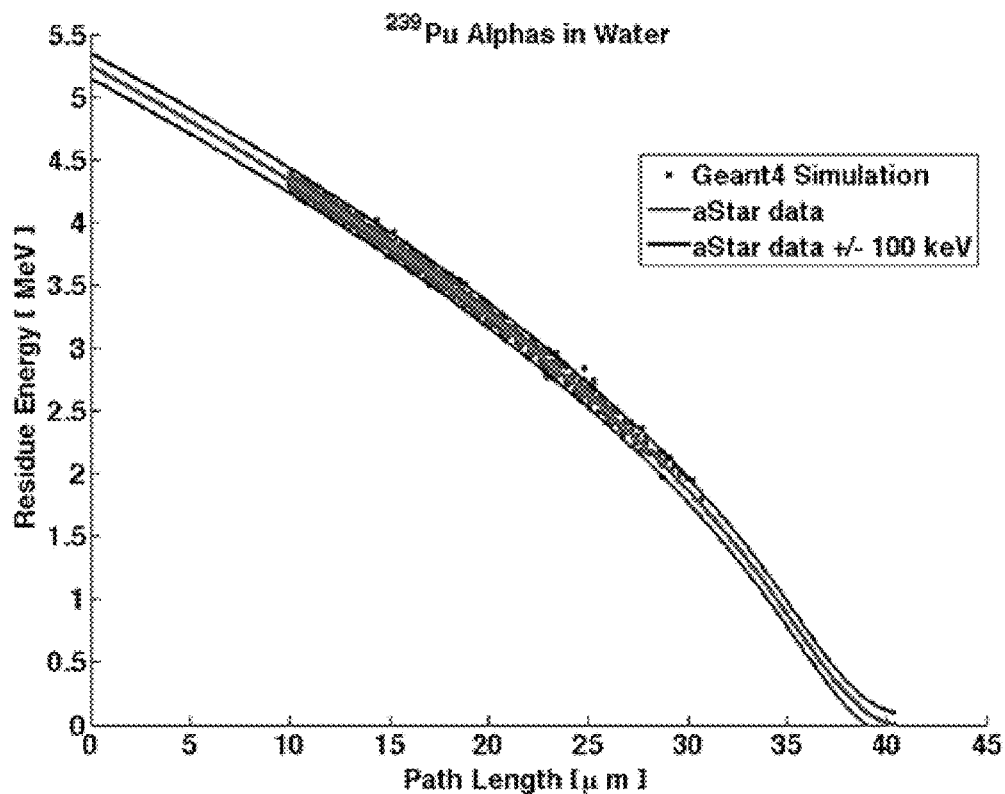
FIG. 10C illustrates the residual energy for $^{239}$PU alpha particles in water as a function of path length.
Figure 10D:
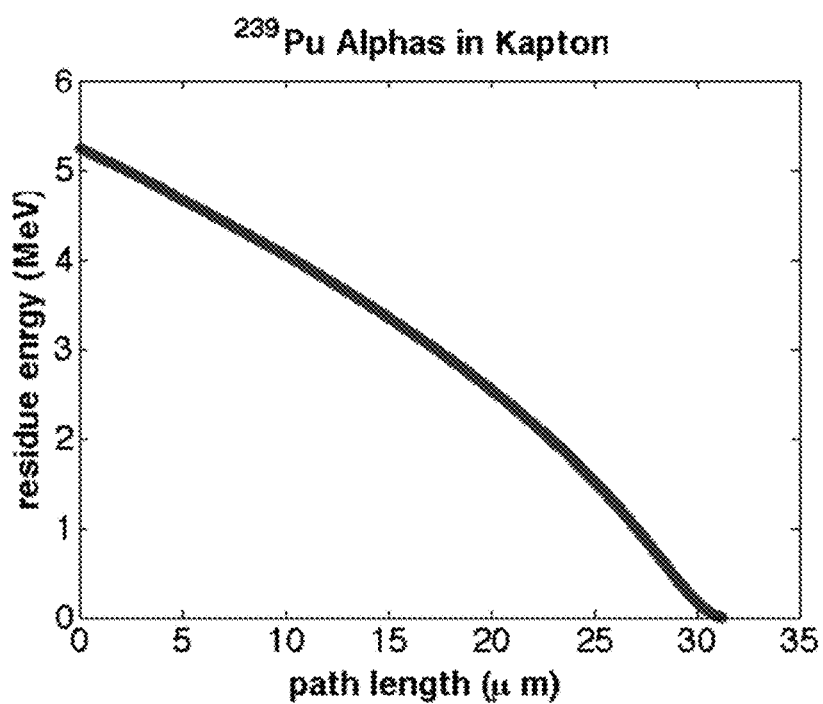
FIG. 10D illustrates the residual energy for $^{239}$PU alpha particles in Kapton as a function of path length.

Unlike beta particles, alpha sources emit particles with a discrete spectrum. Alpha particles interact with matter primarily through Coulomb forces between their positive charge and the negative charge of the orbital electrons within the absorber atoms. Except at their very end, the tracks (particle trajectories) tend to be quite straight, as shown in FIG. 10A-D. FIG. 10A shows Geant4-simulated tracks of $^{239}$Pu alpha particles in water. FIG. 10B shows Δθ as the angular deviation from straight line propagation. The angular deviation of Geant4 simulated data has mean 1.00° and standard deviation 0.28°. FIGS. 10C and 10D show the residual energy for $^{239}$Pu alpha particles in water and Kapton, respectively, as a function of path length.

REFERENCES

M. J. Berger, J. Coursey, M. Zucker, and J. Chang, *Stopping-power and range tables for electrons, protons, and helium ions*. NIST Physics Laboratory, 1998.

L. Caucci, L. Furenlid, and H. Barrett, "Maximum likelihood event estimation and list-mode image reconstruction on GPU hardware," in *IEEE Nuclear Science Symposium Conference Record (NSS/MIC)*, 2009.; and J. Y. Hesterman, L. Caucci, M. A. Kupinski, H. H. Barrett and L. R. Furenlid, "Maximum-likelihood estimation with a contracting-grid search algorithm," IEEE Trans. Nucl. Sci., 57(3), 1077-1084 2010. PMC2932457

J. Jakubek, A. Cejnarova, T. Holy, S. Pospisil, J. Uher, and Z. Vykydal, "Pixel detectors for imaging with heavy charged particles," *Nucl. Instr. and Meth. A*, 2008.

Example 7

Additional Embodiments of Detector Systems

Figure 11A:
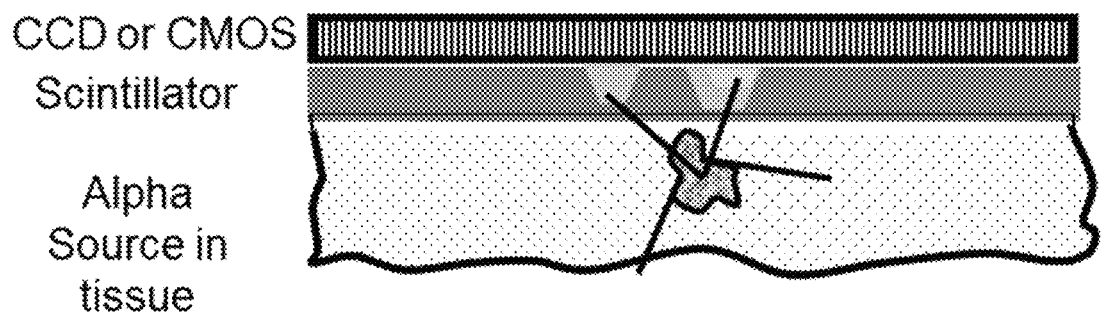
FIG. 11A illustrates an exemplary embodiment of a system for determining the 3D reconstruction of a particle-generating object located within a tissue comprising at least a CCD or CMOS detector and a scintillator.

FIG. 11A illustrates an exemplary embodiment of a scintillation camera for charged particles comprising at least a CCD or CMOS detector and a scintillator.

Figure 11B:
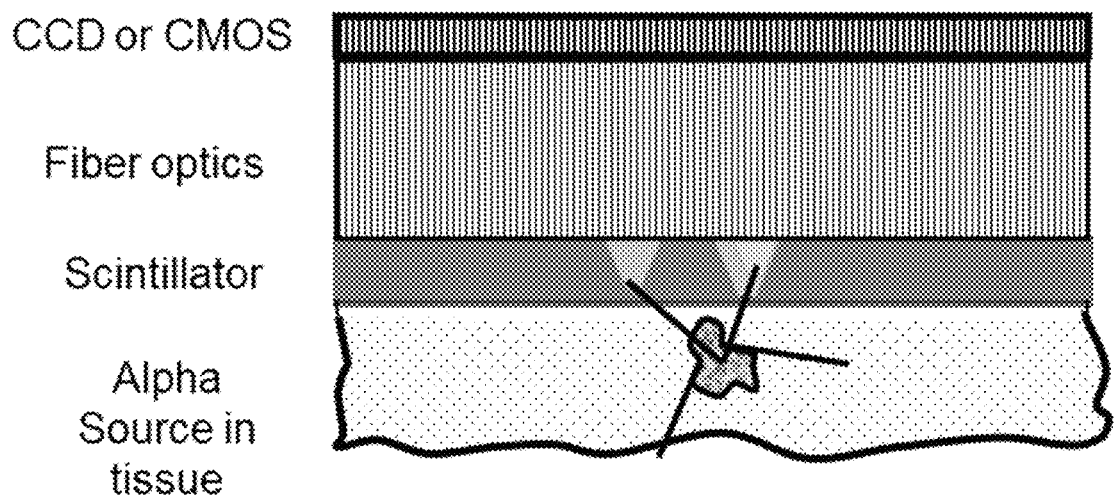
FIG. 11B illustrates an exemplary embodiment of a system for determining the 3D reconstruction of a particle-generating object located within a tissue comprising at least a CCD or CMOS detector, fiber optics, and a scintillator.

FIG. 11B illustrates an exemplary embodiment of a scintillation camera for charged particles comprising at least a CCD or CMOS detector, fiber optics, and a scintillator.

Figure 11C:
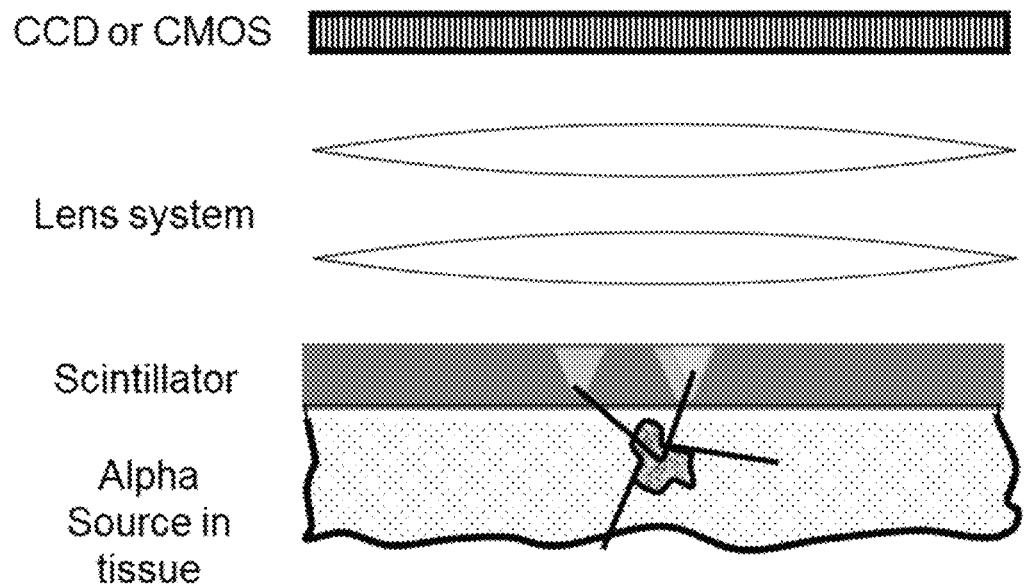
FIG. 11C illustrates an exemplary embodiment of a system for determining the 3D reconstruction of a particle-generating object located within a tissue comprising at least a CCD or CMOS detector, a lens system, and a scintillator.

FIG. 11C illustrates an exemplary embodiment of a scintillation camera for charged particles comprising at least a CCD or CMOS detector, a lens system, and a scintillator.

Figure 11D:
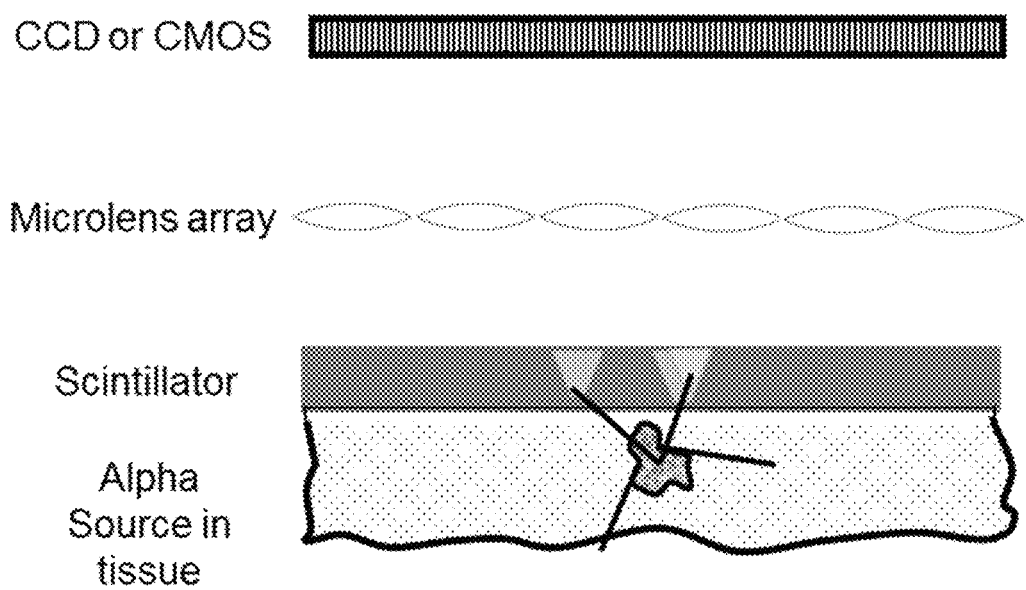
FIG. 11D illustrates an exemplary embodiment of a system for determining the 3D reconstruction of a particle generating object located within a tissue comprising at least a CCD or CMOS detector, a microlens array, and a scintillator.

FIG. 11D illustrates an exemplary embodiment of a scintillation camera for charged particles comprising at least a CCD or CMOS detector, a microlens array, and a scintillator.

Figure 12:
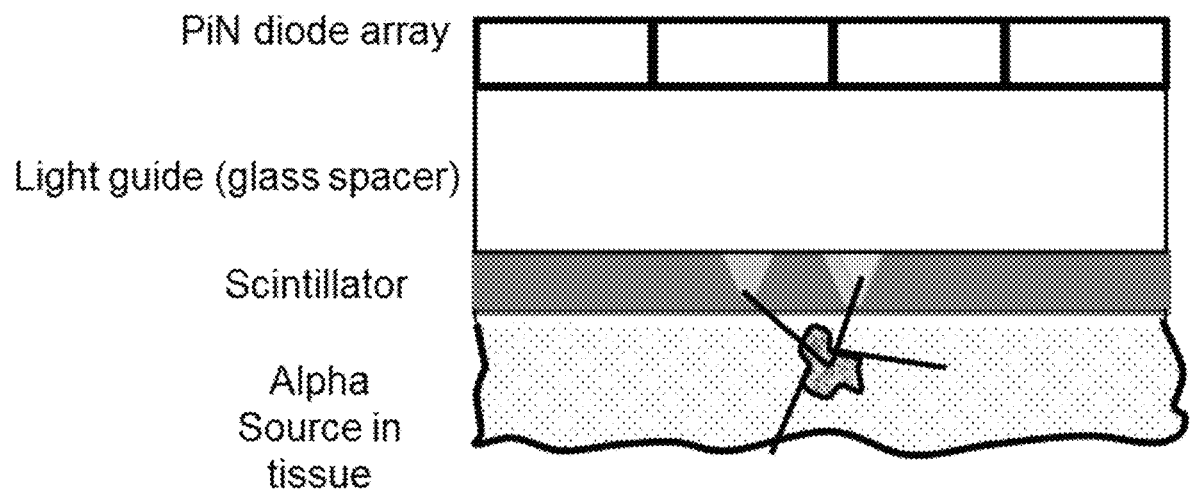
FIG. 12 illustrates an exemplary embodiment of a system for determining the 3D reconstruction of a particle generating object located within a tissue comprising at least a PiN diode array detector, a light guide (glass spacer), and a scintillator.

FIG. 12 illustrates an exemplary embodiment of a scintillation camera for charged particles comprising at least a PiN diode array detector, a light guide (glass spacer), and a scintillator.

Example 8

Particle Detection and Characterization Using Track Detection

Some of the systems and methods of the invention may also be implemented using track detection to provide additional particle characterization complementary to measurements of 2D position and energy deposited in the detector. Suitable track detectors, for example, include scintillator-based detectors, microchannel plate-based image intensifiers coupled to a thick scintillation material, CMOS detectors and CCD detectors. In certain embodiments, for example, the track detector measures a detected image corresponding to particle trajectory, such as an elongated image, which is analyzed to determine attributes of the particle such as the 2D position at which the charged particle entered the detector, the particle's direction at that point (or other points along the particle trajectory in the detector) and/or the total energy deposited in the detector. Use of track detection in the invention, therefore, provides supplemental characterization of particle direction, in addition to of 2D position and energy deposited in the detector, thereby providing additional particle attributes allowing for more accurate and/or efficient reconstruction of the distribution of a source of the particles. In an embodiment, for example, the detector configuration provides a measurement of the direction of the particle at the point of interacting with the detector, for example, comprising two or more angles characterizing a direction of travel along the particle trajectory.

In some embodiments, for example, detected particles interact with an active material, such as a light-emitting or electron-emitting material, so as to generate a track of interactions corresponding to the particle trajectory within the track detector component. The invention includes embodiments, for example, wherein: (i) the thickness of the active material (e.g., light-emitting or electron-emitting material) is selected such that the particle does not traverse the entire thickness of the track detector component or, alternatively, (ii) the thickness of the active material (e.g., light-emitting or electron-emitting material) is thin enough such that the particle does traverse the entire thickness and, optionally impinges directly on a sensor component of the detector configuration; e.g., a CMOS, CDD, or other semiconductor detector.

Detection and characterization of the image of generated by the particle interacting with the active material (e.g., light-emitting or electron-emitting material) at multiple points along the track allows for determination of the direction of travel of the particle, optionally represented as one or more angles, which may be also added to a list, 4D grid or other database for later reconstruction of the distribution of source of the particle. In a specific embodiment, for example, a method of this aspect further comprises the steps of: repeating, for each of a plurality of particles from the source, the steps of: a) recording an image of a particle track with a particle track detector; b) determining attributes of the particle track (e.g., 2D position, direction, trajectory, energy deposited in detector, etc.) using the particle track image; and c) storing the attributes of the particle track; thereby generating additional attributes for each of the plurality of particles from the source. In an embodiment, the attributes of the particle track are determined to within the uncertainty of a selected analytical approach, such as a list-mode maximum likelihood expectation—maximization algorithm. In an embodiment, the attributes of the particle track are estimated, for example, using an approximate analysis technique or predictive algorithm.

Figure 13:
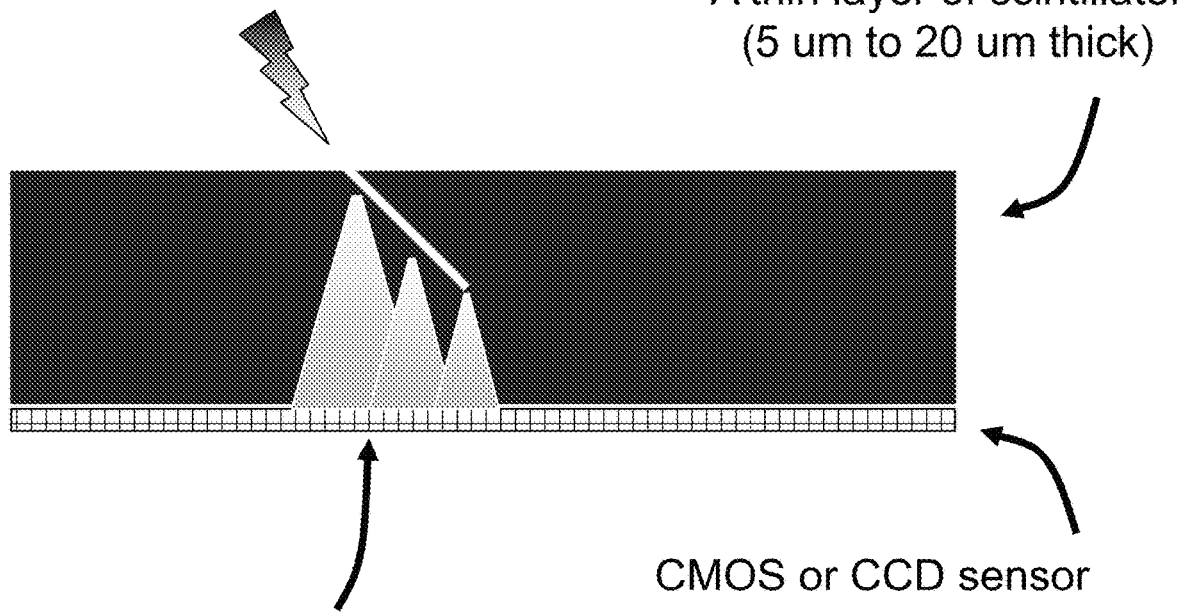
FIG. 13 provides a schematic diagram illustrating a detector configuration for track detection comprising a scintillator layer in optical communication with a CMOS or CCD detector.

FIG. 13 provides a schematic diagram illustrating a detector configuration for track detection comprising a scintillator layer in optical communication with a CMOS or CCD detector. As shown in this figure, a thin layer of scintillator (e.g., 5 µm to 20 µm thick) is provided in close proximity (e.g., with 10 mm or optionally within 1 mm) to the CMOS or CCD detector (or other light sensitive detector). For some applications, the pixel size of the detector is small enough such that light from the particle track is imaged on a plurality of pixels so as to provide a detected image characterized by a shape, such as an elongated shape. Analysis of the shape of the image in some methods and systems provides supplemental information for characterizing attributes the particle, such as the incident direction of the charged particle, as well as the 2D incident position and the energy deposited in the detector.

As shown in this figure, an alpha particle incident to the detector has a trajectory passing through the scintillator, thereby producing scintillation light points along the track. In the embodiment depicted in FIG. 13, the thickness of the scintillator is large enough such that the alpha particle does not entirely pass through the scintillator. As shown in the figure, light originating from interaction points along the track spreads out as a function of distance from the interaction points, thereby generating a more diffuse distribution of radiant intensities. The irradiance on the sensor, therefore, is characterized in some embodiments by an elongated shape, which provides information about the 2D incident position and direction of the charged particle. The cumulative radiant flux provides complementary information useful for characterizing the energy of the charged particle.

Figure 14A:
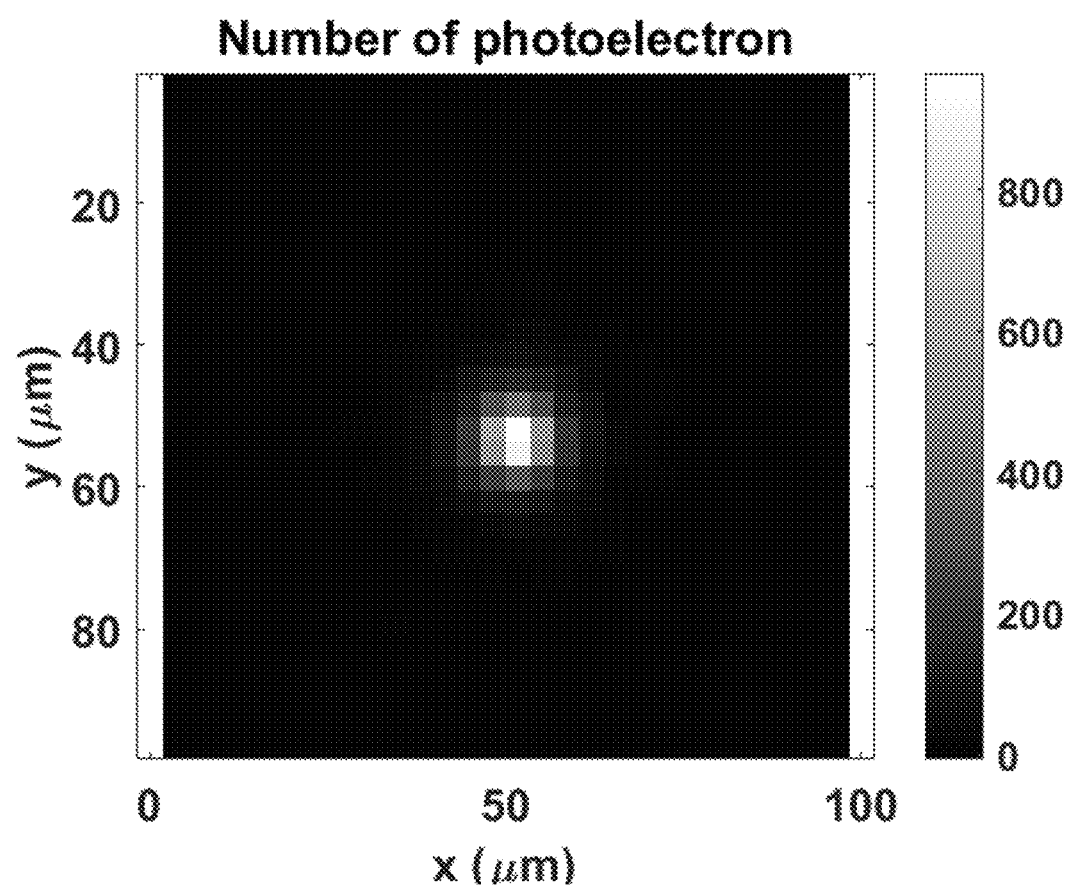
FIG. 14A illustrates a simulated $^{239}$PU alpha decay in a 10 um YAG:Ce scintillator with a Sony IMX 252 CMOS sensor.
Figure 14B:
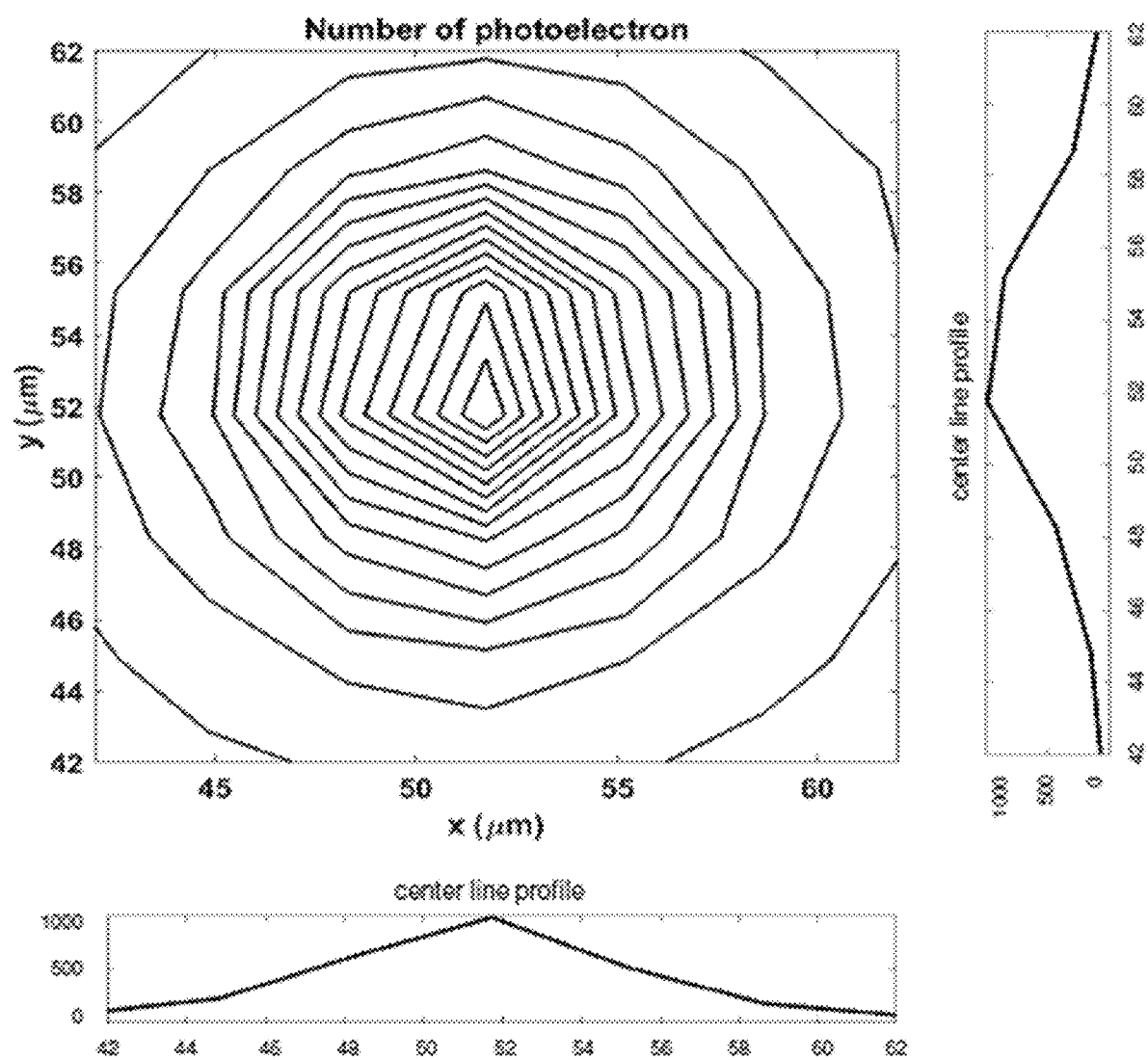
FIG. 14B illustrates a contour plot and center line profiles of the simulated $^{239}$PU alpha decay in a 10 um YAG:Ce scintillator with a Sony IMX 252 CMOS sensor presented in FIG. 14A.

FIG. 14A illustrates a simulated $^{239}$PU alpha decay for a detector configuration comprising a 10 um YAG:Ce scintillator in optical communication with a Sony IMX 252 CMOS sensor. FIG. 14B illustrates a contour plot and center line profiles of the center of the simulated $^{239}$PU alpha decay in a 10 um YAG:Ce scintillator with a Sony IMX 252 CMOS sensor presented in FIG. 14A.

Figure 15:
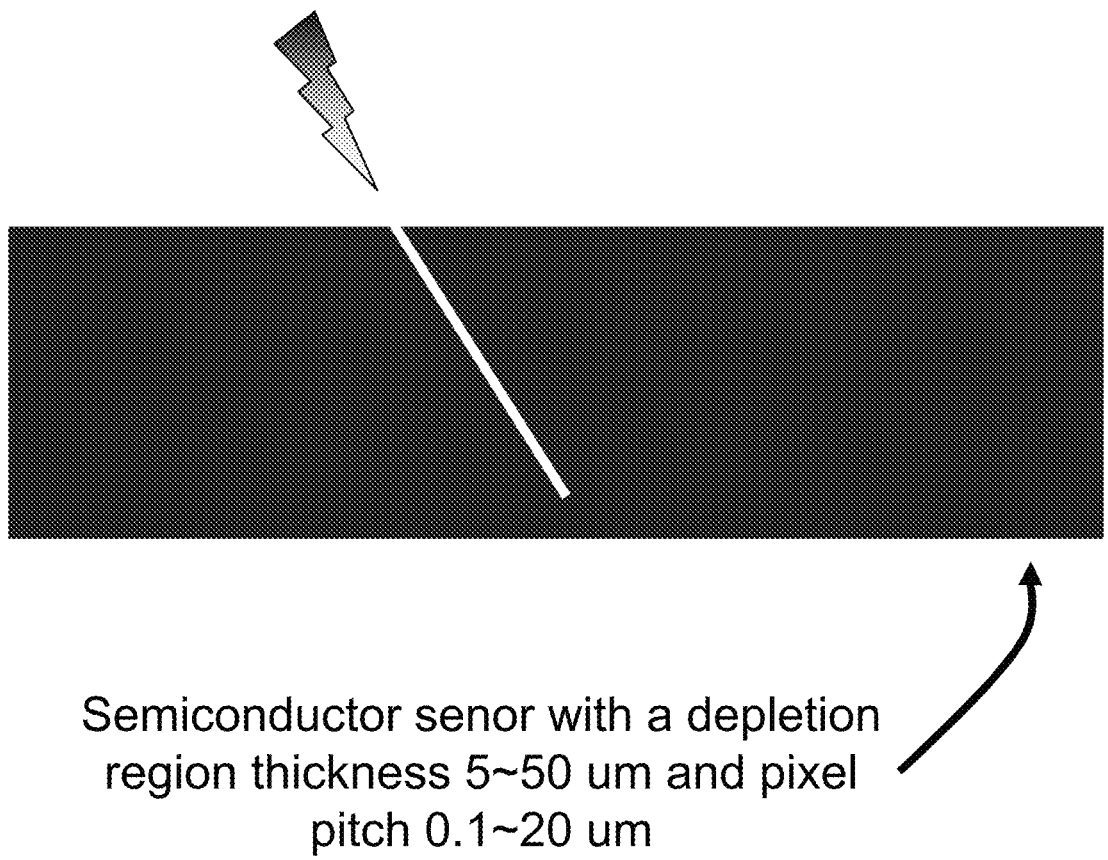
FIG. 15 provides a schematic diagram illustrating a detector configuration for track detection comprising a semiconductor sensor having a depletion region.

FIG. 15 provides a schematic diagram illustrating a detector configuration for track detection comprising a semiconductor sensor having a depletion region. As shown in FIG. 15, an incident alpha particle interacts with the depletion region (e.g. thickness equal to 5 µm-50 µm) of a sensor having a pixel pitch selected from the range of 1 µm to 20 µm, thereby generating charges along its track. The shape of the detected image provides information about the direction of the alpha particle along the particle trajectory and the cumulative intensity of the detected image provides information relating to the energy of the alpha particle. In an embodiment, detection parameters including pixel size and density are selected to allow characterization of the shape of the detected image to allow for characterization of particle direction.

In some embodiments, detector configurations providing track detection may further incorporate optical components such as lenses or an array of lenslets to collect and focus light generated upon a particle passing through a scintillator layer onto a 2D optical sensor such as a CMOS or a CCD detector.

Figure 16:
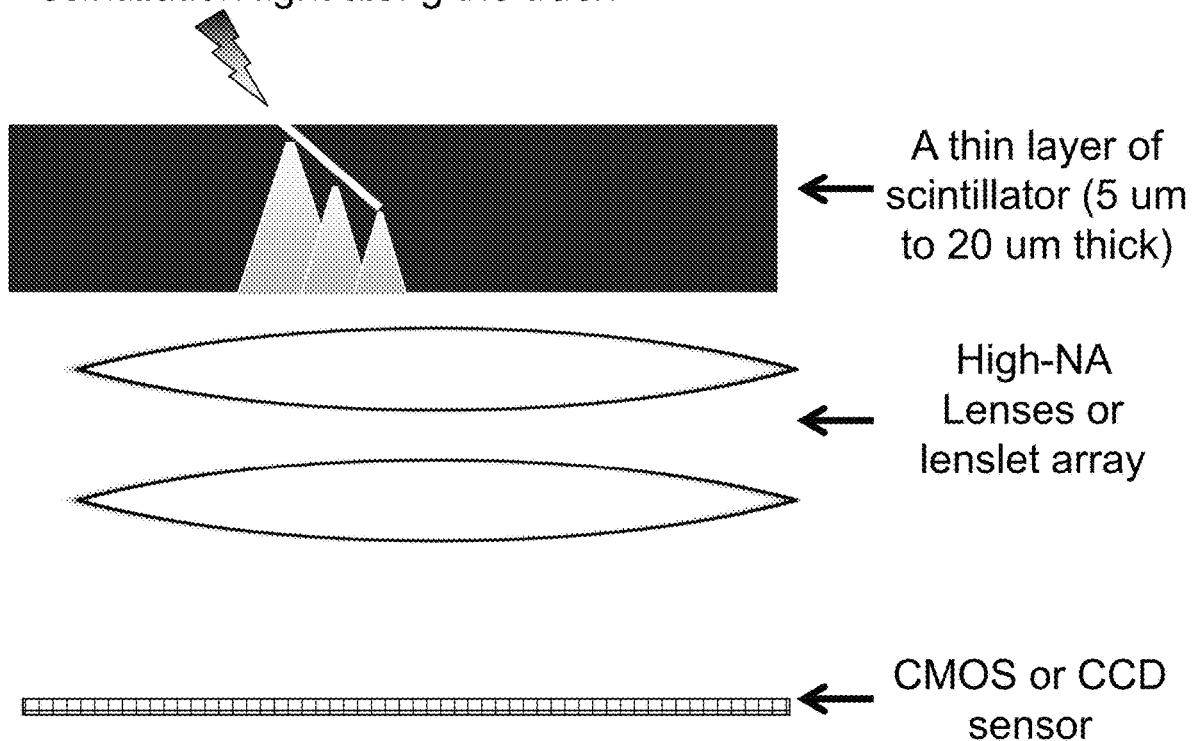
FIG. 16 illustrates a detector configuration for track detection comprising a scintillator layer, high-NA Lenses or lenslet array and a CMOS or CCD detector.
Figure 17:
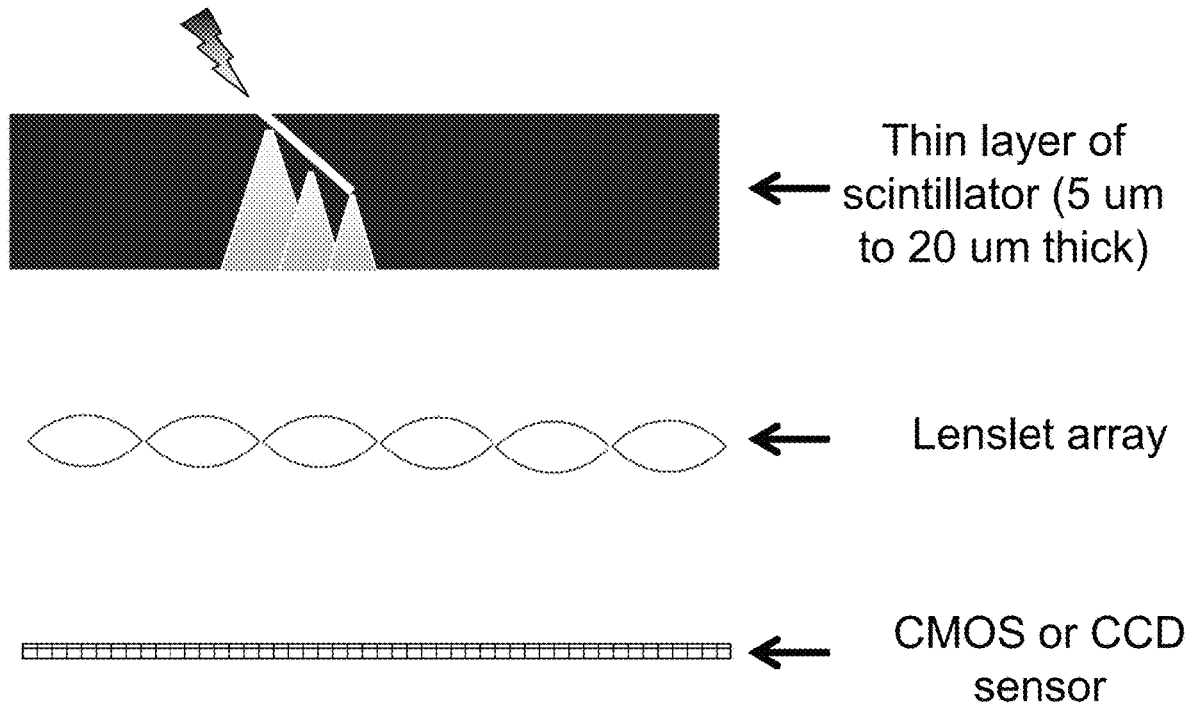
FIG. 17 provides a schematic diagram illustrating detector configuration for track detection comprising a scintillator layer, lenslet array and a CMOS or CCD detector.

FIG. 16 provides a schematic illustration of a detector configuration for track detection comprising a scintillator layer, high-NA Lenses or lenslet array and a CMOS or CCD detector. As shown in this figure, an alpha particle incident into the scintillator layer produces scintillation light along a track corresponding to the trajectory of the particle within the scintillator. In the embodiment depicted in FIG. 16, the thickness of the scintillator is large enough that the alpha particle does not entirely pass through the scintillator. As shown in the figure, light originating from interaction points along the track spreads out as a function of distance from the interaction points, thereby generating a more diffuse distribution of radiant intensities. Light from the scintillator is collected by a lens system and imaged on the CMOS or CCD sensor, thereby generating an image characterized by an elongated shape. Analysis of the elongated image provides for characterization of the incident angle, direction and deposited energy of the particle. FIG. 17 illustrates a detector configuration for track detection comprising a scintillator layer, lenslet array and a CMOS or CCD detector.

Figure 18A:
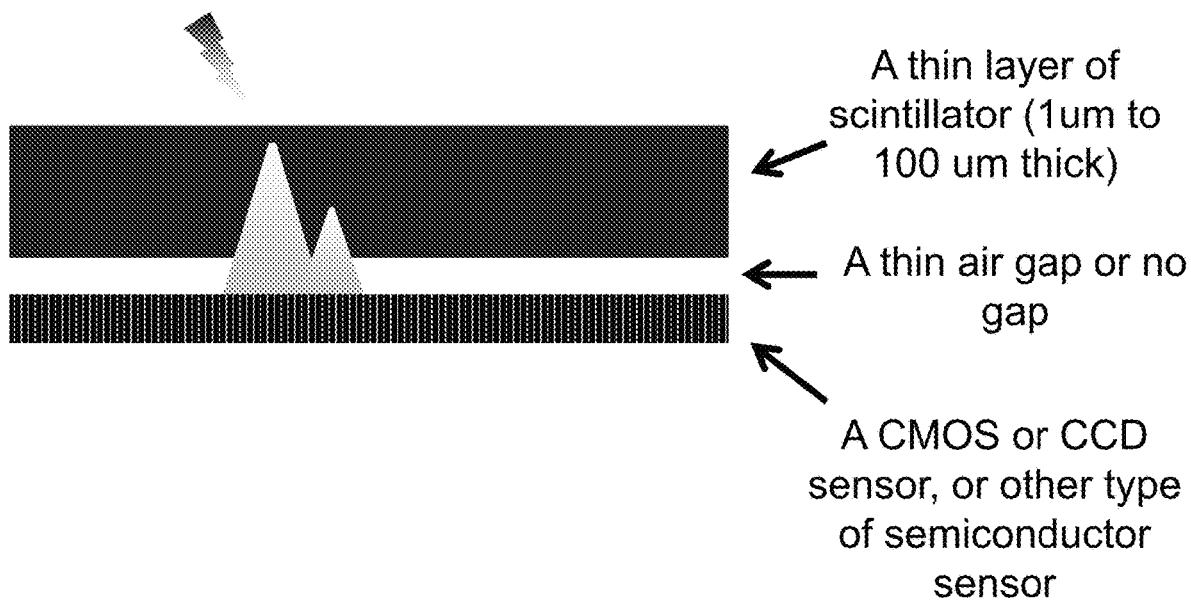
FIG. 18A illustrates a detector configuration for track detection comprising a scintillator layer and a CMOS or CCD detector. Optionally the detector configuration further comprises an air gap provided between scintillator layer and CMOS or CCD detector. The invention include, however, embodiments wherein there is no air gap provided between scintillator layer and CMOS or CCD detector.

In some embodiments, the detector configuration for track detection is arranged such that particles directly interact with both an active material (e.g., light-emitting or electron-emitting material) and a sensor component (e.g., optical, opto-electronic and/or electronic sensor). This aspect of the invention may be particularly well-suited for characterization of particles that are more efficiently and nondestructively transported through components of the detector, such as beta particles. FIG. 18A illustrates a detector configuration for track detection comprising a scintillator layer and a CMOS or CCD detector. Optionally the detector configuration further comprises an air gap provided between scintillator layer and CMOS or CCD detector. The invention include, however, embodiments wherein there is no air gap provided between scintillator layer and CMOS or CCD detector.

Figure 18B:
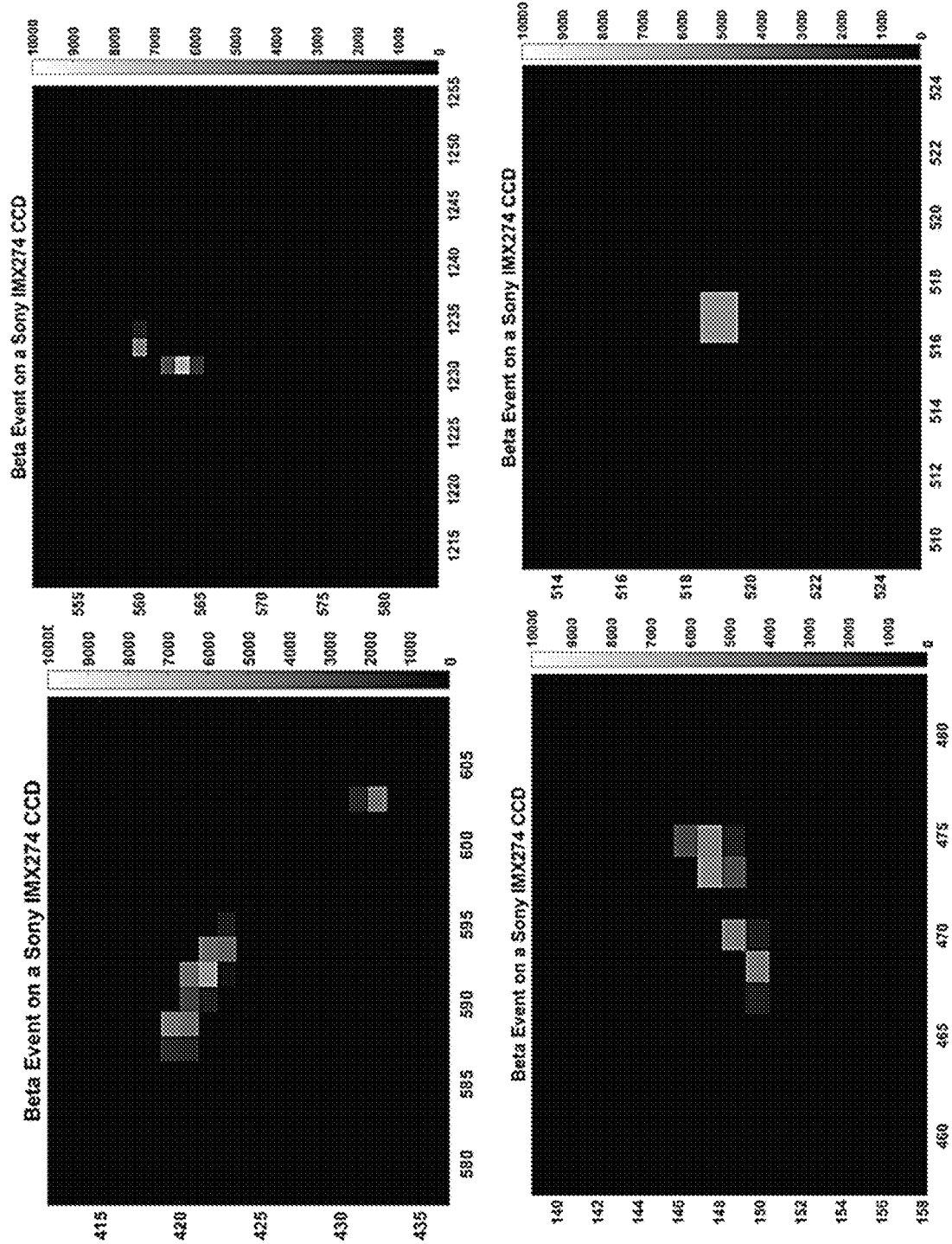

As shown in FIG. 18A, a beta particle penetrates the entire thickness of the scintillator and further directly interacts with the sensor. In this embodiment, the detected image resulting from transport of the particle within the detector is a composite signal comprising a signal component generated by interaction of particle with the scintillator layer and a signal component generated by interaction of particle with the CMOS, CCD or other detector. For example, by combining the signal from the scintillation light and from direct interaction with the CMOS, CCD or other detector, the direction and/or the energy of the particle may be accurately characterized. FIG. 18B provides experimental data of beta particles on a CCD detector without use of a scintillator. FIG. 19 illustrates beta particle tracks detected using a WidePIX detector. The tracks can be analyzed and used for reconstruction of the source distribution.

We claim:

1. A device for reconstructing a 3D distribution of a source of particles from within a tissue sample, wherein the particles comprise beta particles, alpha particles, positrons, or conversion electrons, the device comprising:
    a particle-processing detector for detecting particles;
    a processor positioned in data communication with the particle-processing detector, wherein the processor is configured for:
        determining attributes of the particle; wherein the attributes include:
            (i) a particle interaction time; and
            (ii) energy of the particle upon interacting with the detector;
        and wherein the attributes additionally include at least two of:
            (iii) a two dimensional position corresponding to an interaction point where the particle interacts with the particle-processing detector;
            (iv) an energy that is deposited in the particle-processing detector by the particle; or
            (v) a direction of travel of the particle; and
        storing the attributes of the particle;
    thereby generating attributes for each of a plurality of particles from the source; and
    reconstructing the 3D distribution of the source of particles using at least a portion of the attributes for each of the plurality of particles.

2. The device of claim 1, wherein the processor comprises a computer, or other hardware equivalent implementing a computer software.

3. The device of claim 1, wherein the processor is able to reconstruct the 3D distribution using a tomographic reconstruction algorithm, a particle transport algorithm, or both.

4. The device of claim 1, wherein the processor is able to reconstruct the 3D distribution using a maximum-likelihood algorithm.

5. The device of claim 1, wherein the processor is able to reconstruct the 3D distribution using a list-mode maximum-like expectation-maximization algorithm.

6. The device of claim 1, wherein the processor is able to reconstruct the 3D distribution using an Ordered Subsets-Expectation Maximization (OSEM) algorithm, an Algebraic Reconstruction Technique (ART), or a Simultaneous Iterative Reconstructive Technique (SIRT).

7. The device of claim 1, wherein the particle-processing detector comprises a silicon sensor or a scintillation camera.

8. The device of claim 1, wherein the particle-processing detector comprises a track detector.

9. The device of claim 1, wherein the particle-processing detector further comprises a graphics processing unit (GPU), field-programmable gate array (FPGA), or an application-specific integrated circuit (ASIC).

10. The device of claim 1 comprising a tomographic imaging system.

11. The device of claim 1, wherein the particles comprise alpha particles.

12. The device of claim 1, wherein the attributes further comprise a type of tissue sample that the particle travels through, one or more angles characterizing a direction of travel along an independent particle trajectory at a 2D position, or a 2D position of a start of a particle track.

13. The device of claim 1, wherein the processor is able to reconstruct the 3D distribution using a tomographic reconstruction algorithm, a particle transport algorithm, a maximum-likelihood algorithm, an Ordered Subsets-Expectation Maximization (OSEM) algorithm, an Algebraic Reconstruction Technique (ART), or a Simultaneous Iterative Reconstructive Technique (SIRT).

* * * * *